(12) United States Patent
Molyneux et al.

(10) Patent No.: US 11,519,040 B2
(45) Date of Patent: Dec. 6, 2022

(54) SYSTEM AND METHOD FOR DETECTING PATHOGENS IN AN ENVIRONMENT

(71) Applicant: Poppy Health, Inc., Houston, TX (US)

(72) Inventors: Sam D. Molyneux, Houston, TX (US); Elizabeth Caley, Houston, TX (US); Daniela Bezdan, Houston, TX (US); Ricardo Vidal, Houston, TX (US); Nathan A. Volman, Houston, TX (US); Tae Joon Yi, Houston, TX (US)

(73) Assignee: Poppy Health, Inc., Houston, TX (US)

( * ) Notice: Subject to any disclaimer, the term of this patent is extended or adjusted under 35 U.S.C. 154(b) by 0 days.

(21) Appl. No.: 17/559,257

(22) Filed: Dec. 22, 2021

(65) Prior Publication Data

US 2022/0195536 A1      Jun. 23, 2022

Related U.S. Application Data

(60) Provisional application No. 63/129,263, filed on Dec. 22, 2020.

(51) Int. Cl.
*G01N 1/24* (2006.01)
*G01N 33/00* (2006.01)
(Continued)

(52) U.S. Cl.
CPC .............. *C12Q 1/6888* (2013.01); *A61L 2/10* (2013.01); *A61L 2/24* (2013.01); *A61L 9/20* (2013.01);
(Continued)

(58) Field of Classification Search
CPC .............. G01N 1/2273; G01N 1/2208; G01N 2001/2223; G01N 1/2211;
(Continued)

(56) References Cited

U.S. PATENT DOCUMENTS

| 7,578,973 B2 | 8/2009 | Call et al. |
| 7,633,606 B2 * | 12/2009 | Northrup ............. G01N 1/2273 356/73 |

(Continued)

FOREIGN PATENT DOCUMENTS

| CN | 111662816 A | 9/2020 |
| CN | 112014528 A | 12/2020 |

(Continued)

OTHER PUBLICATIONS

M. Z. Bazant, J. W. Bush, A guideline to limit indoor airborne transmission of covid-19. Proceedings of the National Academy of Sciences. 118 (2021), doi:10.1073/pnas.2018995118.

(Continued)

*Primary Examiner* — David A. Rogers
(74) *Attorney, Agent, or Firm* — Run8 Patent Group, LLC; Peter Miller; Leah Raddatz

(57) ABSTRACT

One variation of a method for detecting pathogens in an environment includes, during a first sampling period: triggering collection of a pathogen sample from ambient air in the environment by an air sampler; and tracking a first organic load of the first pathogen sample via a detection subsystem integrated within the air sampler, the first organic load representative of a first amount of organic matter present in the first pathogen sample. In response to the first organic load exceeding a threshold organic load defined for the environment, the method further includes: interpreting presence of a set of pathogens in the environment via genetic analysis of the first pathogen sample; and, in response to detecting presence of a first pathogen, in the set of pathogens, in the first pathogen sample, transmitting a notification indicating presence of the first pathogen in the environment to a user associated with the environment.

20 Claims, 5 Drawing Sheets

(51) Int. Cl.
*C12Q 1/6888* (2018.01)
*A61L 2/24* (2006.01)
*A61L 2/10* (2006.01)
*A61L 9/20* (2006.01)
*C12Q 1/06* (2006.01)
*C12Q 1/68* (2018.01)
*G01N 33/497* (2006.01)
*C12Q 1/689* (2018.01)
*C12Q 1/6895* (2018.01)

(52) U.S. Cl.
CPC ............... *C12Q 1/06* (2013.01); *C12Q 1/68* (2013.01); *G01N 1/24* (2013.01); *G01N 33/0036* (2013.01); *G01N 33/0075* (2013.01); *G01N 33/497* (2013.01); *A61L 2202/11* (2013.01); *A61L 2202/14* (2013.01); *A61L 2209/11* (2013.01); *A61L 2209/12* (2013.01); *A61L 2209/14* (2013.01); *C12Q 1/689* (2013.01); *C12Q 1/6895* (2013.01)

(58) Field of Classification Search
CPC ....... G01N 2001/2276; G01N 15/0606; G01N 2015/0088
See application file for complete search history.

(56) References Cited

U.S. PATENT DOCUMENTS

| | | | |
|---|---|---|---|
| 8,173,431 B1 * | 5/2012 | Call | G01N 1/2208 436/104 |
| 8,272,280 B2 * | 9/2012 | Jones, Jr. | A22B 5/007 73/31.02 |
| 8,539,840 B2 * | 9/2013 | Ariessohn | G01N 1/2202 73/860 |
| 8,578,796 B2 * | 11/2013 | Cho | G01N 1/2205 73/28.01 |
| 8,689,648 B1 * | 4/2014 | Heff | G01N 1/2273 73/863.22 |
| 9,689,792 B1 * | 6/2017 | Sickenberger | G01N 21/00 |
| 10,919,047 B2 * | 2/2021 | Mainelis | B03C 3/41 |
| 11,300,484 B1 * | 4/2022 | Bango | G01N 1/24 |
| 2011/0252897 A1 * | 10/2011 | Swenson | G01N 1/2208 73/863 |
| 2012/0174650 A1 * | 7/2012 | Ariessohn | G01N 1/2202 73/23.2 |
| 2021/0208062 A1 * | 7/2021 | Linden | G01N 21/3504 |
| 2021/0324485 A1 * | 10/2021 | Hodges | C12N 15/1017 |
| 2022/0034763 A1 * | 2/2022 | Dutta | G01N 1/2205 |
| 2022/0091010 A1 * | 3/2022 | Wystup | G01N 15/06 |

FOREIGN PATENT DOCUMENTS

| | | | |
|---|---|---|---|
| JP | 2017096727 A | * | 6/2017 |
| KR | 20110097199 A | * | 8/2011 |
| WO | 2019018559 A1 | | 1/2019 |
| WO | WO-2022047340 A1 | * | 3/2022 |
| WO | WO-2022081543 A1 | * | 4/2022 |

OTHER PUBLICATIONS

International Search Report and Written Opinion for International Patent Application No. PCT/US2021/64875 dated Mar. 29, 2022; 13 pages.

* cited by examiner

SYSTEM AND METHOD FOR DETECTING PATHOGENS IN AN ENVIRONMENT

CROSS-REFERENCE TO RELATED APPLICATIONS

This Application claims the benefit of U.S. Provisional Application No. 63/129,263, filed on 22 Dec. 2020, which is incorporated in its entirety by this reference.

TECHNICAL FIELD

This invention relates generally to the field of metagenomics and more specifically to a new and useful method for pathogen detection in the field of metagenomics.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
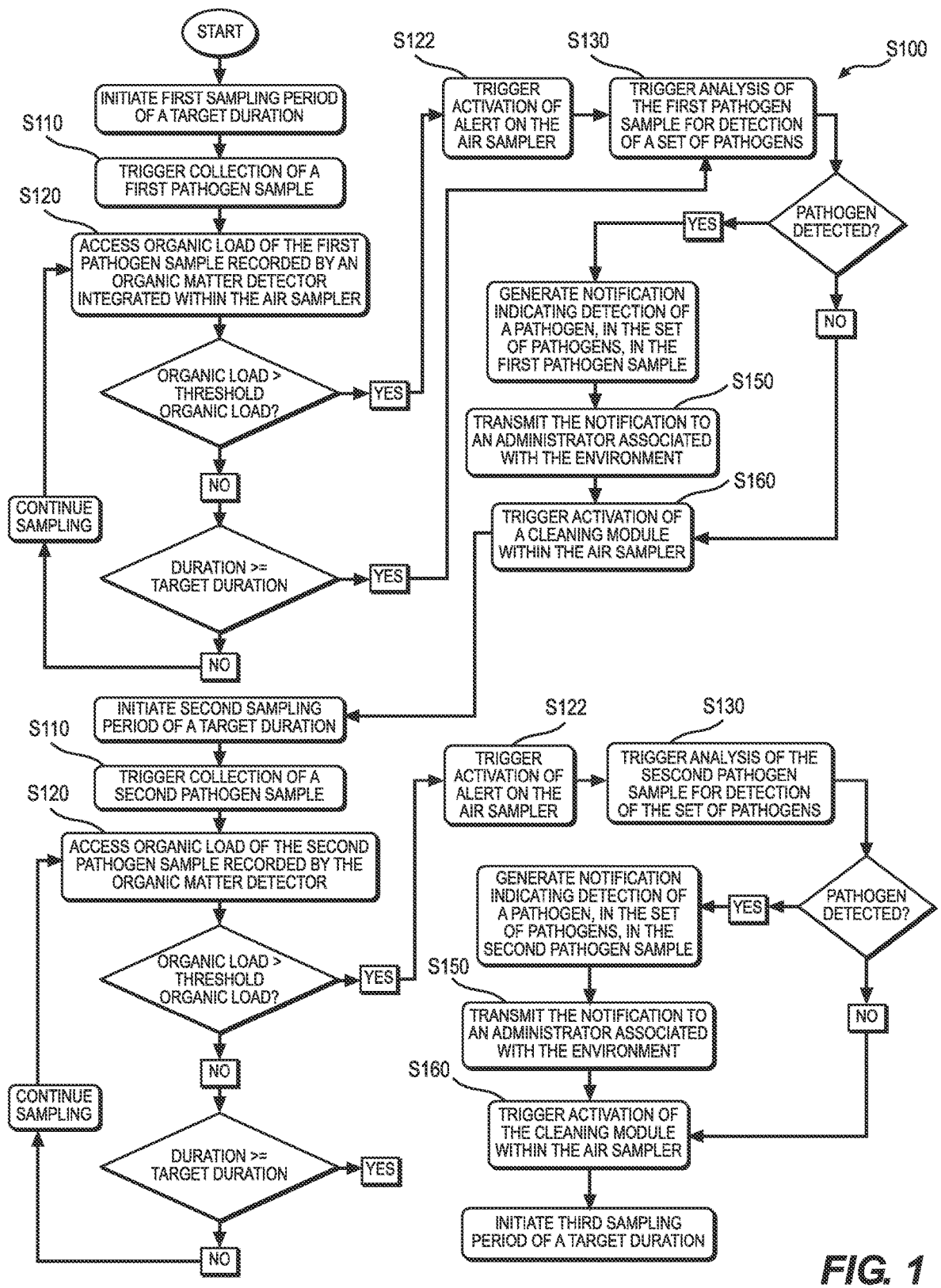
FIG. 1 is a flowchart representation of a method.
Figure 2:
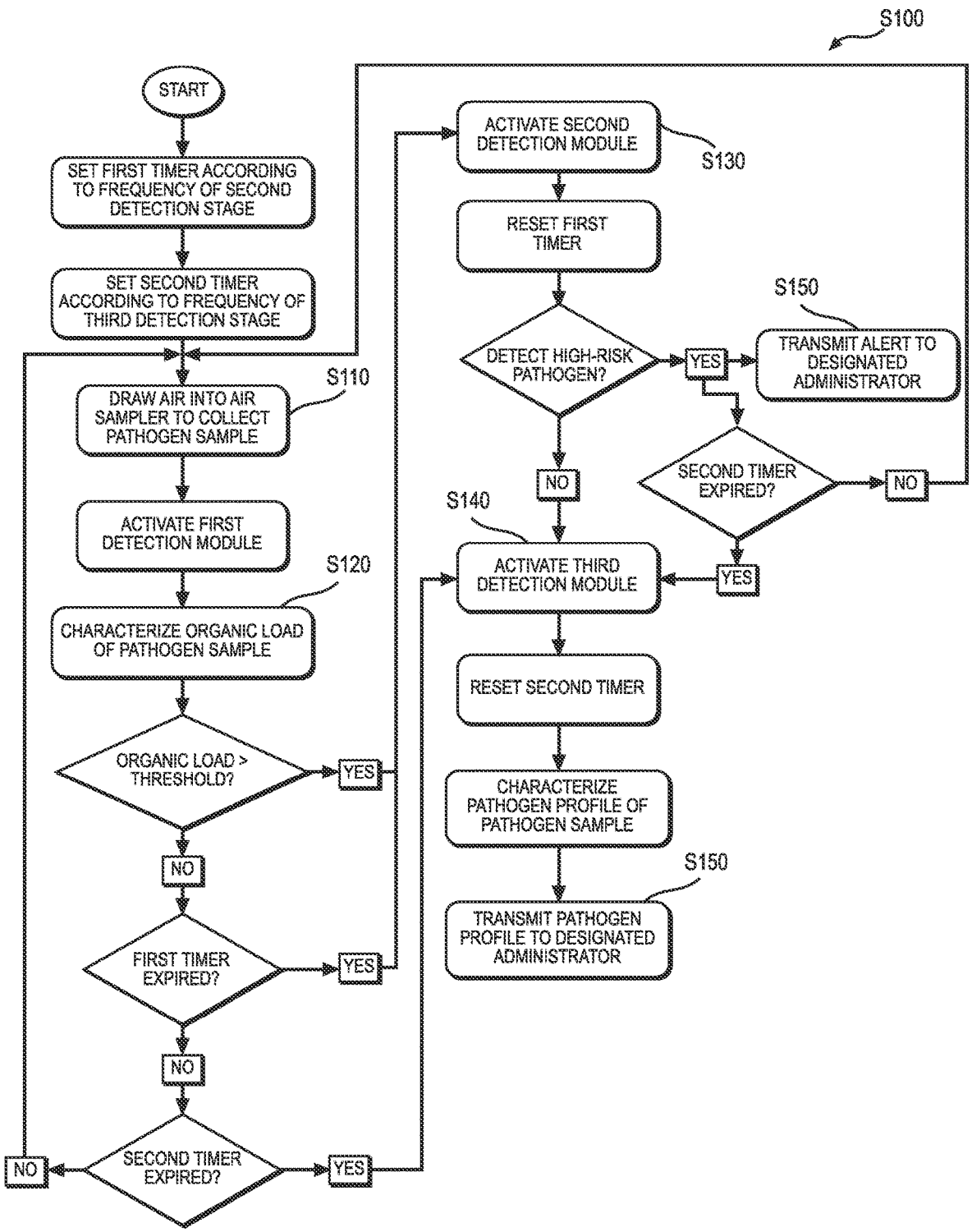
FIG. 2 is a flowchart representation of the method.
Figure 3:
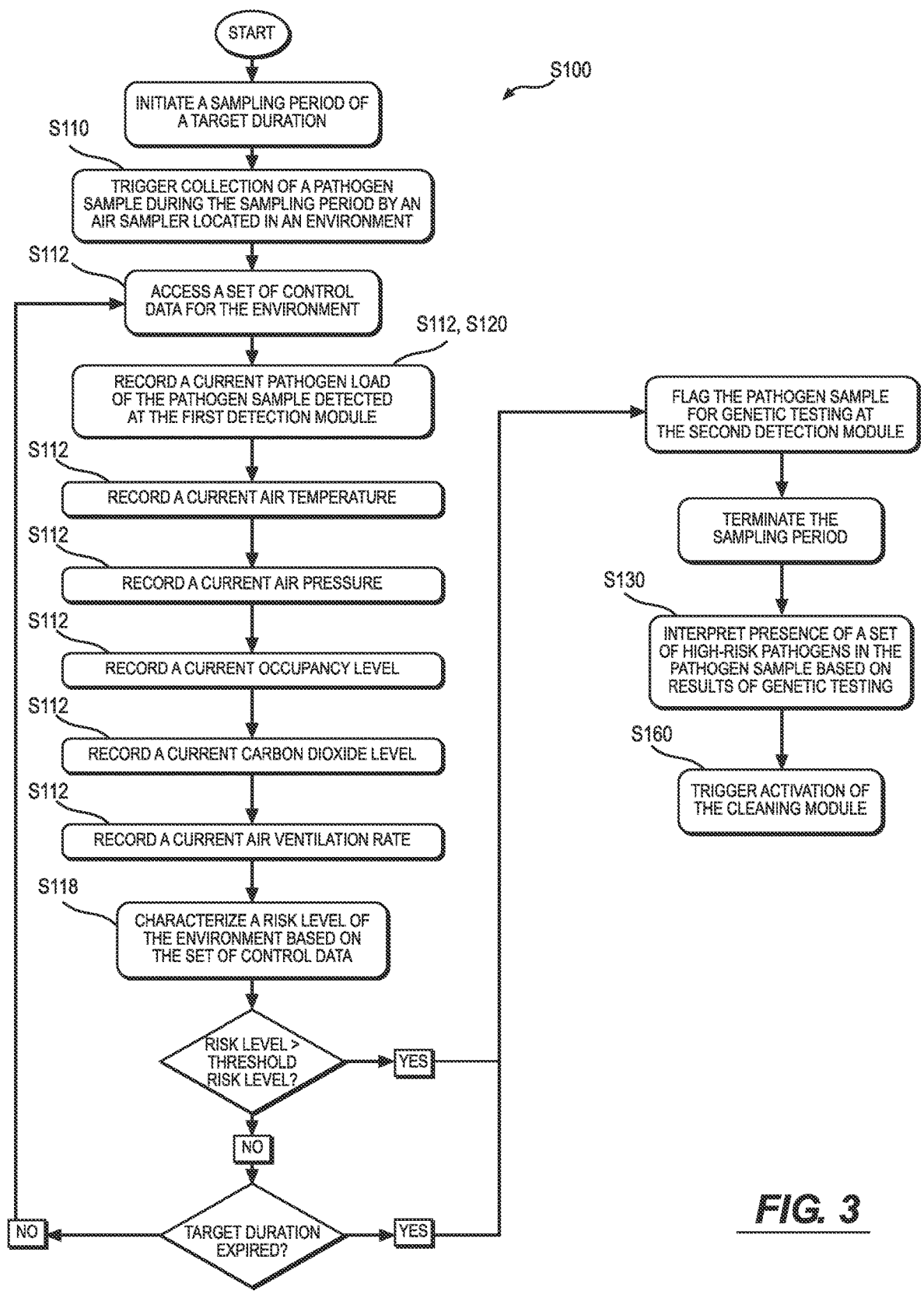
FIG. 3 is a flowchart representation of the method.
Figure 4:
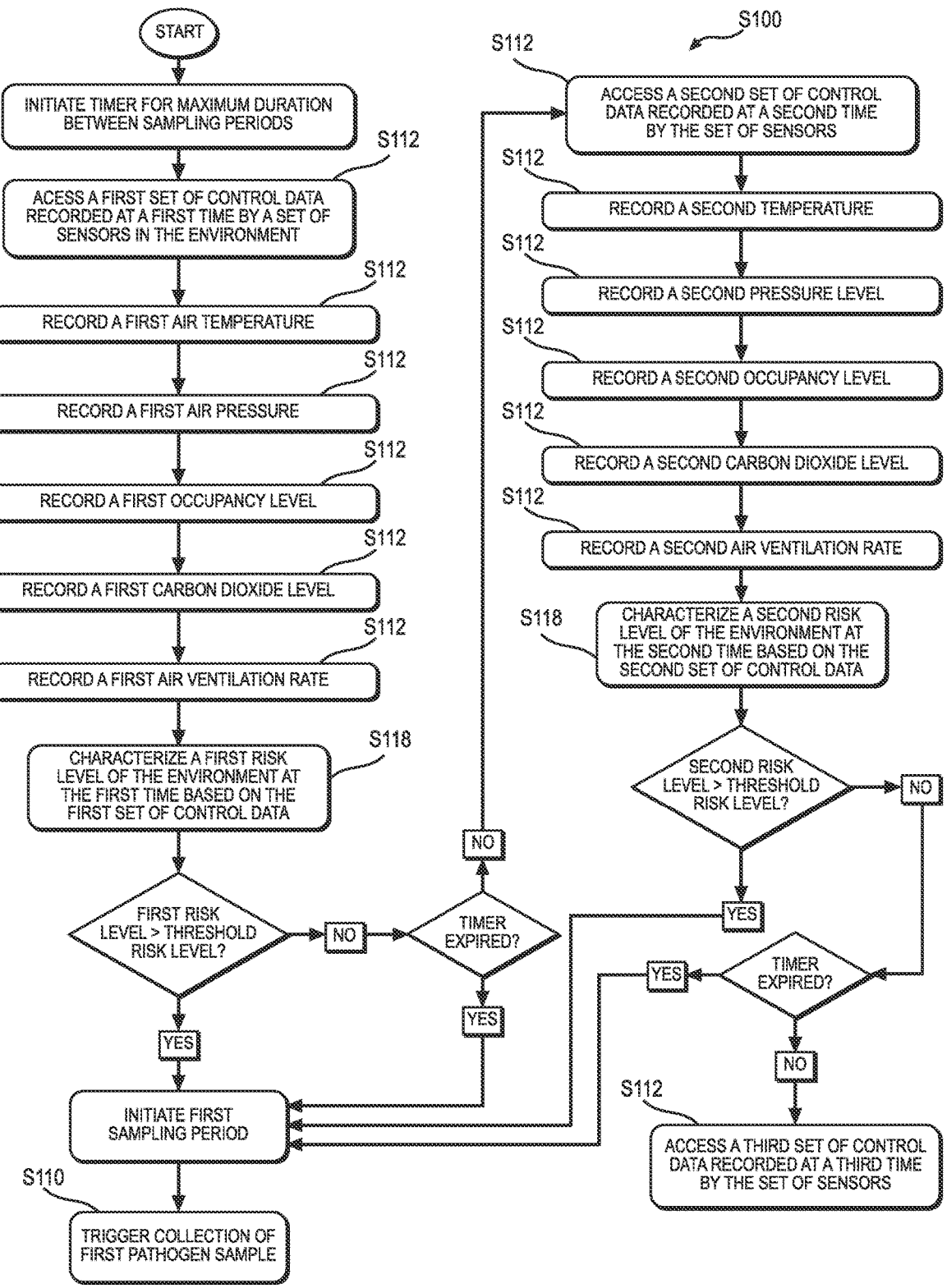
FIG. 4 is a flowchart representation of the method.
Figure 5A:
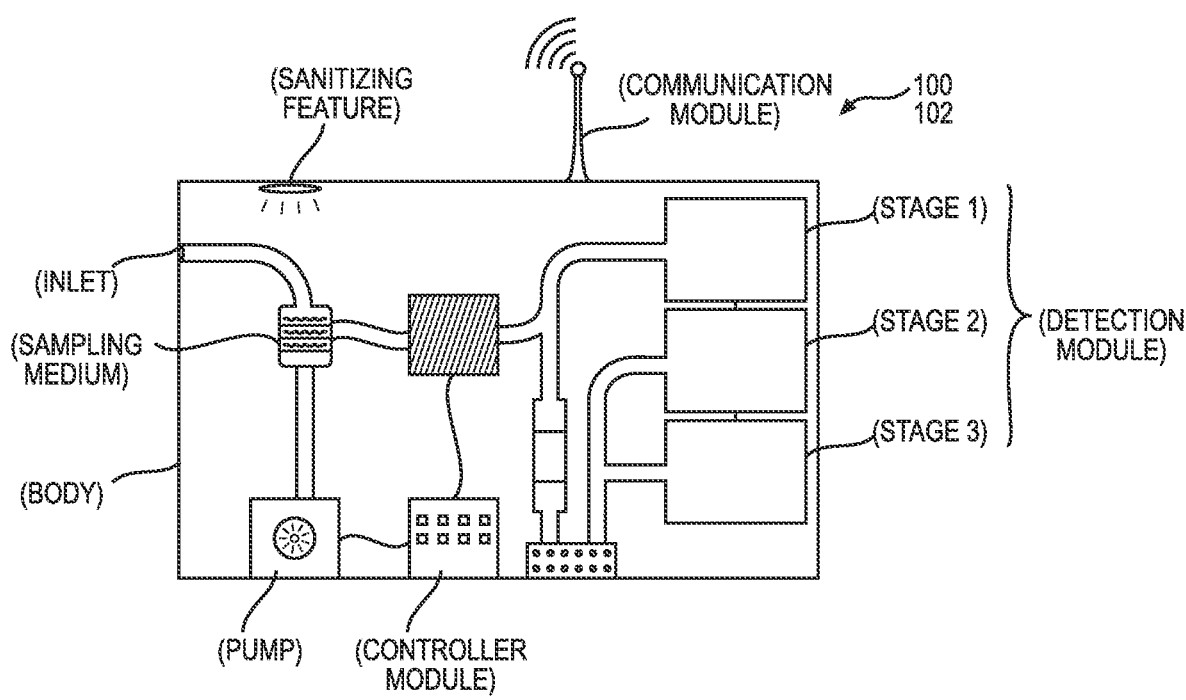
FIGS. 5A and 5B are schematic representations of a system.
Figure 5B:
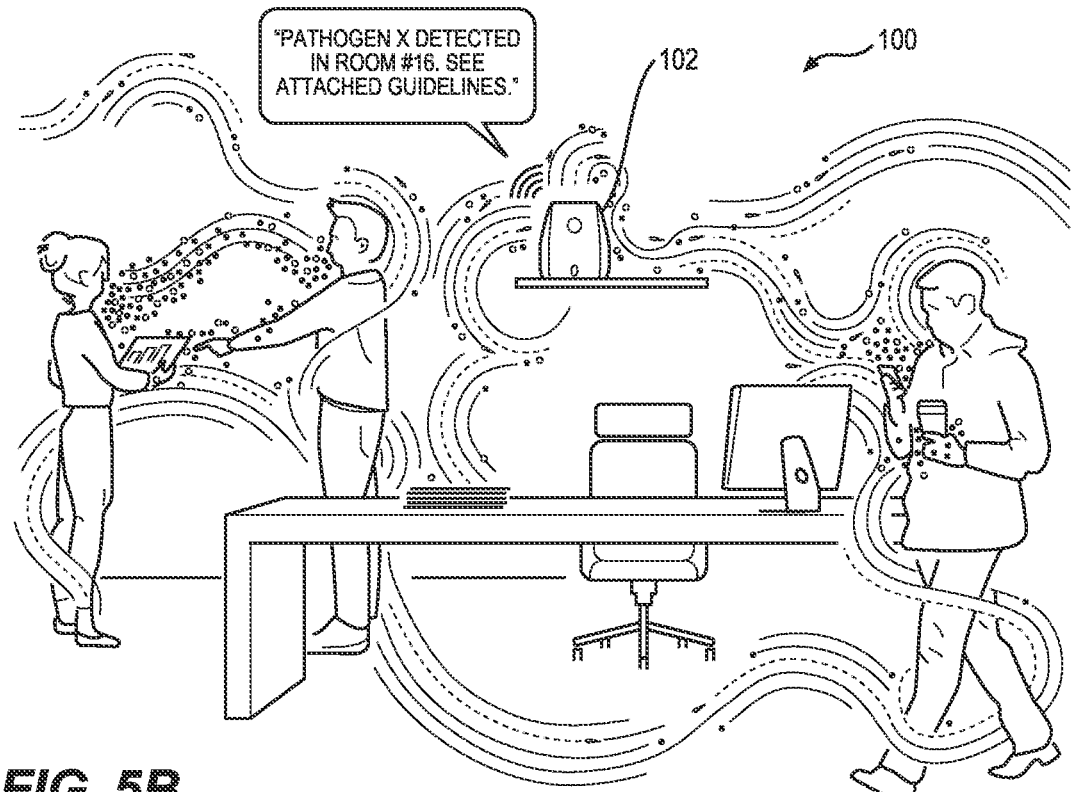

As shown in FIGS. 1-4, a method S100 for detecting pathogens in an environment includes, during a first sampling period of a target duration: triggering collection of a first pathogen sample by an air sampler 102 located in the environment and configured to draw ambient air from the environment through an inlet of the air sampler 102 and onto a sampling medium within the air sampler 102 for collection of pathogen samples in Block Silo; and tracking a first organic load of the first pathogen sample via a first detection module integrated within the air sampler 102 and configured to detect organic matter present in pathogen samples in Block S120. The method S100 further includes, during the first sampling period, in response to the first organic load exceeding a threshold organic load defined for the environment: flagging the first pathogen sample for further investigation; interpreting presence of a set of pathogens in the environment based on genetic analysis of the first pathogen sample via a second detection module configured to detect presence of the set of pathogens in pathogen samples via genetic analysis in Block S130; and, in response to detecting presence of a first pathogen, in the set of pathogens, in the first pathogen sample, generating a first notification indicating presence of the first pathogen in the environment and transmitting the first notification to a set of users associated with the environment in Block S150.

In one variation, the method S100 further includes, in response to terminating the first sampling period, triggering activation of a cleaning module within the air sampler 102 during a first cleaning cycle, the cleaning module configured to sanitize surfaces of the air module to prevent contamination of pathogen samples in Block S160.

In one variation, the method S100 further includes, in response to the first organic load exceeding the threshold organic load, activating a second notification indicating detection of an organic load anomaly in the environment in Block S122.

In one variation, the method S100 further includes: accessing a set of control data corresponding to the environment and recorded by a set of sensors arranged within the environment in Block S112; and characterizing a risk level in the environment for detection of a particular set of pathogens based on the set of control data.

One variation of the method S100 includes, during a first sampling period of a first target duration: triggering collection of a first pathogen sample from ambient air in the environment at an air sampler 102 configured to draw ambient air from the environment, through an inlet of the air sampler 102, and onto a sampling medium loaded in the air sampler 102 for collection of pathogen samples in Block Silo; and tracking a first organic load of the first pathogen sample via a detection module integrated within the air sampler 102 in Block S120. In response to the first organic load exceeding a threshold organic load defined for the environment prior to expiration of the first target duration, the method S100 further includes: terminating the first sampling period; and interpreting presence of a set of pathogens in the environment via genetic analysis of the first pathogen sample in Block S130.

In this variation, the method S100 further includes, during a second sampling period of a second target duration: triggering collection of a second pathogen sample from ambient air in the environment at the air sampler 102 in Block Silo; tracking a second organic load of the second pathogen sample in Block S120; and, in response to the second organic load remaining below the threshold organic load prior to expiration of the second target duration, continuing triggering collection of the second pathogen sample. In response to expiration of the second target duration, the method S100 further includes: terminating the second sampling period; and interpreting presence of the set of pathogens in the environment via genetic analysis of the second pathogen sample in Block S130.

One variation of the method S100 includes, during a first sampling period: triggering collection of a first pathogen sample from ambient air in the environment at an air sampler 102 configured to draw ambient air from the environment, through an inlet of the air sampler 102, and onto a sampling medium loaded in the air sampler 102 for collection of pathogen samples in Block Silo; and tracking a first organic load of the first pathogen sample via a detection subsystem integrated within the air sampler 102, the first organic load representative of a first amount of organic matter present in the first pathogen sample in Block S120. In response to the first organic load exceeding a threshold organic load defined for the environment, the method S100 further includes: flagging the first pathogen sample for further investigation; interpreting presence of a set of pathogens in the environment via genetic sequencing of the first pathogen sample in Block S140; and, in response to detecting presence of a first pathogen, in the set of pathogens, in the first pathogen sample, generating a notification indicating presence of the first pathogen in the environment and transmitting the notification to a user associated with the environment in Block S150.

One variation of the method S100 includes, during a first air sampling period, drawing an air stream from an environment through an inlet of an air sampler 102 for collection of a pathogen sample from the air stream in Block Silo; and, in a first detection stage of the air sampler 102, estimating an organic load of the pathogen sample in Block S120. The method further includes, during the first air sampling period, in response to characterizing the organic load of the pathogen sample above a threshold organic load: activating a second detection stage of the air sampler 102 configured to detect presence of a first set of pathogens in Block S130; and, in response to detecting presence of a first pathogen, in the first set of pathogens, in the pathogen sample, transmitting a notification to a user associated with the environment in Block S150. The method further includes, in response to detecting absence of the first set of pathogens from the pathogen sample: activating a third detection stage of the air sampler 102 configured to identify a pathogen profile of the pathogen sample in Block S140; and, in response to the pathogen profile specifying presence of a second pathogen in the pathogen sample, transmitting a notification to the user associated with the environment in Block S150.

2. System

As shown in FIGS. 5A and 5B, an air sampler 102 includes: a body; an inlet; an air-capture module; a sampling medium; a detection subsystem; a controller module; a communication module; and a cleaning module.

The body is configured to house: the air-capture module; the sampling medium; the detection subsystem; the controller module; and the communication module.

The inlet is defined by the body and is configured to pass air from the environment into the body.

The air-capture module (e.g., a pump) is configured to draw air from the environment (e.g., an enclosed room, an interior space), through the inlet of the body, toward the sampling medium.

The sampling medium (e.g., a cartridge, a charged plate) is configured to collect an air sample—including bioaerosols (e.g., viruses, bacteria, fungi)—for concentrating over a sampling period.

The detection subsystem is configured to: receive the air sample from the sampling medium; and characterize presence of pathogens in the air sample via genetic testing.

The controller module includes a set of electronics configured to selectively actuate components of the air sampler 102.

The communication module is configured to transmit data and/or notifications from the air sampler 102 between the pathogen detection system 100 and a set of external devices (e.g., a mobile device, a computing device) and/or a computer system (e.g., a local server, a remote computer system).

The cleaning module is configured to: sanitize the sampling medium in preparation for pathogen sample collection; and sanitize the pathogen sample in preparation for handling by a user.

In one variation, the air sampler 102 further includes an air-directing device configured: to direct airflow within the environment in which the pathogen detection system 100 is located; to encourage distribution and/or movement of airborne particles in the environment; and/or to direct air within the environment toward the inlet of the body. For example, the air directing device can be a fan or a blower.

In one variation, the air sampler 102 further includes an external sanitization feature configured to sanitize the environment occupied by the pathogen detection system 100.

3. Applications

Generally, Blocks of the method S100 can be executed by or in conjunction with a pathogen detection system 100: to identify pathogens present in a pathogen sample extracted from an external environment (e.g., an enclosed space within a building) occupied by the air sampler 102; to interpret presence of and/or magnitude of pathogens present in the pathogen sample; and to selectively generate and distribute prompts related to detection of these pathogens and/or mitigating pathogens detected in the external field.

The pathogen detection system 100 can extract pathogen samples from the external field and process these samples to identify pathogens present in the external field. Based on changes in pathogen levels and/or identification of particular pathogens in the external field, the pathogen detection system 100—in combination with a computer system (e.g., a local computing device, a remote server, a computer network)—can interpret pathogen risk for this external field and communicate this risk and/or suggest a mitigation technique to a user associated with the external field.

The air sampler 102 can be deployed to a particular environment (e.g., an office building, a restaurant, an airplane, a school) and can directly sample air from this environment and locally implement pathogen detection concurrently across multiple detection stages (or "detection modules") according to the method S100. For example, the air sampler 102 can: autonomously operate a non-specific, continuous microbe detector at the anomaly detection module to detect generic microbe levels or concentrations within an air sample (nearly) continuously; autonomously operate a selective, high-risk pathogen detector at the pathogen-specific detection module to intermittently detect specific pathogen detection at the pathogen-specific detection module; and autonomously operate a genetic sequencer at the pathogen-profile detection module to intermittently calculate a pathogen profile within an air sample. Further, the pathogen detection system 100 can include a communication module configured to transmit data and/or notifications to an authority associated with the environment. Therefore, the air sampler 102—in combination with the pathogen detection system 100—can identify and detect pathogens in the environment and alert an appropriate authority in near-real time to enable rapid mitigation of pathogens detected in the environment.

In particular, the pathogen detection system 100 can (nearly) continuously pass a sample—extracted ambient air captured from the external field—through a anomaly detection module to derive a high-frequency, (near) real-time time series of microbe levels in the air in the external field. The pathogen detection system 100 can also intermittently pass a sample—extracted ambient air captured from the external field—through a pathogen-specific detection module to detect select pathogens (e.g., "pathogens of interest") in the air in the external field and to derive a moderate-frequency, intermittent time series of levels of these select pathogens in the air in the external field. Furthermore, the pathogen detection system 100 can intermittently pass a sample—extracted ambient air captured from the external field—through a pathogen-profile detection module to identify genomes of many (or all detectable) microbes present in the air in the external field and to derive a low-frequency, high-resolution time series of levels of these microbes in the air in the external field.

The pathogen detection system 100 can thus combine low-resolution, high-frequency time series of non-specific microbe levels in the external field with higher-resolution, lower-frequency time series of specific pathogens of interest and/or all genomes in the external field to confirm, identify, and/or predict pathogen presence in the external field. More specifically, the pathogen detection system 100 can be configured to identify: changes in ambient microbe levels in air in the external field nearly continuously (e.g., at a frequency of 1 Hz); presence of a particular pathogen (e.g., a virus of interest, a bacteria of interest) in the air in the external field on a longer time interval (e.g., once per hour or when triggered by the first stage); and/or a pathogen profile (e.g., a microbiome and corresponding genome levels (or counts, concentrations) of the air in the external environment on a longer time interval (e.g., twice per hour or when triggered by the first and/or second stages).

Therefore, the pathogen detection system 100 can be deployed inside an office, a restaurant, a museum, a transporting terminal, a home, a venue, and/or other indoor, enclosed, or semi-enclosed environment to: rapidly detect rises in airborne microbe levels; quickly detect presence and levels of particular pathogens of interest (e.g., up to five high-risk bacterium or viruses); detect presence of all airborne microbes (at concentrations above a minimum detectable level); and to selectively generate and return notifications for responding to risk associated with presence and levels of such airborne microbes in the space. The pathogen detection system 100 can therefore execute Blocks of the method S100 to automatically monitor airborne microbes surrounding air over a range of resolutions and frequencies, to estimate risk to nearby occupants based on these airborne microbes, and to return reports or notifications to these occupants or another entity affiliated with this environment in order to manage such risk to these occupants.

4. Example

In one example, the pathogen detection system 100 can be installed in a conference room of an office building. The pathogen detection system 100 can include a handoff module configured to pass pathogen samples collected at the sampling medium to the detection subsystem. In this example, the handoff module can include: a first handoff configured to transfer pathogen samples—extracted from air in the conference room at a first frequency—to an anomaly detection module of the pathogen detection system 100; a second handoff configured to transfer pathogen samples—extracted from air in the conference room at a second frequency less than the first frequency—to a pathogen-specific detection module of the pathogen detection system 100; and a third handoff configured to transfer pathogen samples—extracted from air in the conference room at a third frequency less than the first and second frequency—to a pathogen-profile detection module of the pathogen detection system 100.

In particular, at a first time, the pathogen detection system 100 can: actuate a fan proximal or coupled to the body to blow ambient air from the environment into and/or toward the inlet; and actuate a pump to draw ambient air from the inlet onto the sampling medium configured to collect bioaerosols in air to generate a first pathogen sample. The pathogen detection system 100 can continue to draw air for the first pathogen sample into the inlet over a first sampling period of a relatively short duration (e.g., 30 seconds, one minute, ten minutes)—designated for the anomaly detection module—to concentrate bioaerosols present in the first pathogen sample within the anomaly detection module. In the anomaly detection module, the pathogen detection system 100 can include an adenosine triphosphate (or "ATP") detector configured to characterize an organic load (e.g., based on a quantity of ATP present) of the first pathogen sample, which may be indicative of a total quantity of living organisms in bioaerosols that are present in the conference room. If the organic load exceeds a threshold organic load defined for this conference room, the pathogen detection system 100—in combination with the computer system—can alert a user(s) of this increased organic load. In this example, the pathogen detection system 100 can trigger activation of an external light, visible to a person(s) present in the conference room, indicating detection of the increased organic load in bioaerosols in the conference room.

Further, in response to the organic load exceeding a threshold organic load in the conference room, the pathogen detection system 100 can trigger activation of the pathogen-specific detection module of the detection subsystem in order to identify a source (e.g., a particular pathogen) of the increased organic load detected in the anomaly detection module. The air sampler 102 can pass the pathogen sample to the pathogen-specific detection module via the second handoff. In this example, the second stage can include a genetic test-kit configured to perform loop-mediated isothermal amplification to detect presence of a set of predefined pathogens in the pathogen sample. In response to detecting a particular predefined pathogen, in the set of predefined pathogens, the pathogen detection system 100 can automatically notify a manager associated with the conference room of the particular predefined pathogen. Further, the pathogen detection system 100 can suggest an action to the manager for mitigating presence of the particular predefined pathogen.

Alternatively, in response to detecting absence of the set of predefined pathogens, the pathogen detection system 100 can trigger activation of the pathogen-profile detection module of the detection subsystem in order to identify a complete pathogen profile of the pathogen sample. In this example, the pathogen-profile detection module can include a genetic sequencer (e.g., a full-spectrum genetic sequencer) configured to identify a genome of each pathogen present in the pathogen sample for identification. The pathogen detection system 100 can compile each identified pathogen (e.g., presence and/or magnitude of each identified pathogen) into a pathogen profile for the pathogen sample. The pathogen detection system 100 can then notify the manager of the pathogen profile and include any suggested actions for mitigating pathogens present in the environment. Further, the pathogen detection system 100 can leverage the complete pathogen profile from the pathogen-profile detection module to confirm data from the first and pathogen-specific detection modules.

5. Deployment

In one implementation, the air sampler 102 can be installed at a particular location within an environment (e.g., fixed to a wall, mounted on a stand, standing on a floor). Alternatively, the air sampler 102 can include a mobile apparatus (e.g., a manual or autonomously cart, an autonomous aerial vehicle) configured to transport the air sampler 102 about the environment. For example, the air sampler 102 can be mounted (e.g., transiently, permanently) to a mobile robot (e.g., a UGV) configured to autonomously navigate between different rooms within an office building to monitor pathogen levels across each of these rooms.

Yet alternatively, the pathogen detection system 100 can include a set of air sampler 102s 102 installed throughout the environment (e.g., one per floor in an office building). For example, the pathogen detection system 100 can include a docking station (e.g., a charging docking station) configured to house a set of air sampler 102s 102, such that each air sampler 102 can be deployed from the docking station to a particular region (e.g., an office) within an environment (e.g., an office building).

6. Air Sampler

The pathogen detection system 100 can trigger the air sampler 102 to collect and concentrate a pathogen sample within the air sampler 102 during a sampling period. In particular, the air sampler 102 can be configured to draw ambient air from the surrounding environment through an inlet of the air sampler 102 and onto a sampling medium (e.g., a cartridge, a surface) loaded within the air sampler 102 for collection of pathogen samples.

The air sampler 102 can therefore include: an inlet configured to pass air from the environment into the air sampler 102; a sampling medium (e.g., a cartridge, a charged plate) configured to collect a pathogen sample—including bioaerosols (e.g., viruses, bacteria, fungi)—for concentrating over a sampling period; and an air-capture module configured to draw air from the environment (e.g., an enclosed room, an interior space), through the inlet of the body, toward the sampling medium. In one implementation, the sampling medium can be replaceable, such that the pathogen detection system 100 includes a set of sampling media configured to be loaded into the air sampler 102.

Additionally, in one implementation, the air sampler 102 includes a detection subsystem including a set of detection modules configured to characterize a composition of a pathogen sample collected by the air sampler 102.

The air sampler 102 can also include: a controller module including a set of electronics configured to selectively actuate components of the air sampler 102; and a communication module configured to transmit data and/or notifications from the air sampler 102 between the pathogen detection system 100, the detection subsystem, a set of external devices (e.g., a mobile device, a computing device) and/or a computer system (e.g., a local server, a remote computer system).

The air sampler 102 can also include a body (or "housing") configured to house the air-capture module, the sampling medium, the controller module, and the communication module.

6.1 Air Capture Module

The air sampler 102 includes an air-capture module configured to draw air through the inlet of the body of the air sampler 102 for collecting a pathogen sample on the sampling medium.

In one implementation, the air sampler 102 includes an air-capture module including a pump coupled to the inlet of the body and configured to draw air from the inlet and onto the sampling medium within the body at a target rate (e.g., once cubic foot per second). This "pump-based air sampler 102" can include a sampling medium in the form of a filter cartridge (e.g., a PTFE filter cassette). For example, the pump-based air sampler 102 can actuate the pump to draw air through the inlet and through the filter cartridge such that particles in the air collect on a filter within the filter cartridge. The pump-based air sampler 102 can continue to actuate the pump to dry and thus concentrate these particles on the filter over a sampling period, such as of a predefined duration (e.g., 30 seconds). Upon expiration of the sampling period, the pathogen detection system 100 can further process the pathogen sample thus collected on the filter in order to prepare the pathogen sample for genetic testing in the detection subsystem.

In another implementation, the air sampler 102 can include an air-capture module configured to draw air from the environment through the inlet of the body via electrostatic forces. This "electrostatic air sampler 102" can include: a charging element; a sampling media in the form of a collector plate; and a power supply air-capture module configured to apply a voltage across the collector plate. For example, the electrostatic air sampler 102 can include: an inlet configured to transfer a pathogen sample from a surrounding area into the electrostatic air sampler 102; a collector plate configured to receive the pathogen sample and collect pathogens present in the pathogen sample; and a corona wire configured to cooperate with the collector plate to draw the pathogen sample through the inlet via electrostatic forces. In particular, the pathogen detection system 100 can be configured to supply a voltage between the corona wire and the collector plate to enable ionization of particles present in the pathogen sample, thereby accelerating these particles through the inlet and onto the collector plate.

In this implementation, the electrostatic air sampler 102 can apply (e.g., drip, spray) a liquid coating (e.g., a saline solution) onto the collector plate before or during a sampling period. The electrostatic air sampler 102 can thus concentrate microbial pathogen samples within the liquid coating rather than directly on the collector plate, thereby enabling post-processing of these microbial pathogen samples for (near) real-time pathogen detection at the anomaly detection module. Once the pathogen sample is collected on the collector plate after the sampling period, the air sampler 102 can be configured to further process the pathogen sample to prepare a DNA and/or RNA library for genetic sequencing according to various genetic techniques.

6.2 Detection Subsystem

The pathogen detection system 100 can include a detection subsystem configured to receive pathogen samples collected within the air sampler 102 for composition analysis (e.g., organic matter detection, genetic testing, genetic sequencing) of these pathogen samples. The detection subsystem can include a set of detection modules, each detection module, in the set of detection modules, configured to perform analysis of a pathogen sample to detect information related to composition of the pathogen sample at different levels of abstraction. For example, the detection subsystem can include a set of detection modules including: a first detection module (or an "anomaly detection module") configured to detect changes in organic matter levels (e.g., relative a baseline organic matter level, relative a preceding organic matter level) in pathogen samples over time; a second detection module (or a "pathogen-specific detection module") configured to detect a set of predefined pathogens (e.g., high-risk pathogens) via genetic testing of pathogen samples; and/or a third detection module (or a "pathogen-profile detection module") configured to identify a complete pathogen profile for a particular pathogen sample via genetic sequencing of the pathogen sample.

In one implementation, the air sampler 102 can be configured to directly process pathogen samples for pathogen detection within the air sampler 102. In particular, the air sampler 102 can include a detection subsystem—directly integrated within the air sampler 102—configured to receive the pathogen sample from the air-capture module for testing. In this implementation, the air sampler 102 can include a handoff configured to transfer a collected pathogen sample from the air-capture module (e.g., from the sampling medium) to the detection subsystem for pathogen detection. In particular, the air sampler 102 can: draw air from the environment through the inlet and onto the sampling medium to collect and enrich a pathogen sample over a sampling period; and, at an expiration of the sampling period, transfer the pathogen sample to the detection subsystem via the handoff.

The detection subsystem can include a processing stage configured to process the pathogen sample in preparation for diagnostics and/or genetic sequencing. For example, at an expiration of a sampling period, the air sampler 102 can be configured to transfer a pathogen sample from the sampling medium to the processing stage of the detection subsystem. At the processing stage, the air sampler 102 can: lyse DNA and/or RNA fragments in the pathogen sample; concentrate these DNA and/or RNA fragments within the pathogen sample; and compile these fragments from the pathogen sample into a genetic library (e.g., a DNA and/or RNA library) for genetic sequencing. The pathogen sample—now prepared into the genetic library—can then be passed through a genetic sequencer (e.g., a nanopore genetic sequencer, a LAMP reactor) configured to identify a set of pathogens present in the pathogen sample.

Alternatively, in another implementation, the pathogen detection system 100 can be configured to capture pathogen samples within the air sampler 102 for further processing and analysis by a remote detection subsystem at a remote location (e.g., in a laboratory, in a genetic testing facility). In this variation, the pathogen sample can be collected at the sampling medium within the air sampler 102 and stored in a storage module within the air sampler 102 for later collection. For example, upon expiration of a sampling period for a pathogen sample, the pathogen detection system 100 can: trigger the air sampler 102 to transfer the pathogen sample (e.g., on or within the sampling medium) from the air-capture module to the storage module; prompt a user associated with the environment (e.g., the environment containing the air sampler 102) to collect the pathogen sample from the storage module, such as within a particular time period succeeding the sampling period; and prompt the user to deliver the pathogen sample to a remote facility for analysis by the detection subsystem located in the remote facility.

Alternatively, in yet another implementation, the pathogen detection system 100 can be configured to capture pathogen samples within the air sampler 102 for further processing and analysis by a local detection subsystem separated from the air sampler 102 and located within the environment and/or within a facility containing the environment. For example, the pathogen detection system 100 can include: an air sampler 102 deployed within a particular room of a facility; and a detection subsystem deployed within the particular room of the facility. In this example, the pathogen detection system 100 can trigger the air sampler 102 to collect a pathogen sample during a sampling period. Then, in response to termination of the sampling period, the pathogen detection system 100 can: prompt a user associated with the environment (e.g., the environment containing the air sampler 102) to collect the pathogen sample (e.g., housed within a cartridge) from the air sampler 102, such as within a particular time period succeeding the sampling period; and prompt the user to transfer the pathogen sample into the detection subsystem—within the same room as the air sampler 102—for further analysis of the pathogen sample.

Additionally and/or alternatively, in yet another implementation, the set of detection modules of the detection subsystem can be distributed in different locations. In particular, the detection subsystem can include the set of detection modules including: a first detection module housed within the air sampler 102; a second detection module external the air sampler 102 and located in an environment containing the air sampler 102; and/or a third detection module external the air sampler 102 and located in a remote location distinct from the environment containing the air sampler 102.

6.2.1 First Detection Module: Anomaly Detection

In one implementation, the pathogen detection system 100 can be configured to detect anomalies in microbe levels (e.g., microbe concentration, quantity of microbes) in the environment. In this implementation, the air sampler 102 can include the detection subsystem including a first detection module (or "anomaly detection module") configured to receive the pathogen sample for monitoring and detecting changes in microbe levels in pathogen samples extracted from the environment. In particular, the detection subsystem can include an organic matter detector (e.g., a microbe detector, an ATP detector) configured to detect presence and/or quantity of organic (i.e., living) matter within the environment (e.g., a conference room in an office, a dining room in a restaurant) occupied by the air sampler 102. The air sampler 102 can be configured to operate the organic matter detector at a relatively high frequency to enable near real-time detection of changes in quantity of organic matter present in the environment in near real-time, which may be indicative of changes in microbe levels within the environment. The pathogen detection system 100 can therefore leverage these detected changes in the quantity of organic matter in the environment to predict changes in microbe levels within the area.

For example, the air sampler 102 can be installed in a conference room of an office building. The air sampler 102 can be configured to continuously draw air from the conference room onto the sampling medium over a sampling period of a particular duration (e.g., 1 minute, 5 minutes, 30 minutes) to collect and concentrate a pathogen sample. Upon expiration of the sampling period, the air sampler 102 can transfer the pathogen sample to the detection subsystem including the anomaly detection module (e.g., within the air sampler 102). Alternatively, the air sampler 102 can be configured to activate the anomaly detection module—arranged proximal and/or within the sampling medium loaded in the air sampler 102—at a particular frequency (e.g., once-per-second, once-per-minute, once every ten minutes, once-per-hour) during the sampling period, such that the pathogen detection system 100 can track an amount of organic matter (or an "organic load") present in the pathogen sample throughout the sampling period.

At the anomaly detection module, the pathogen detection system 100 can: estimate a quantity of ATP in the pathogen sample (e.g., via UV LED detection); and characterize an organic load of the pathogen sample based on the quantity of ATP. The pathogen detection system 100 can then estimate a microbe level (e.g., a magnitude) of the pathogen sample based on the organic load. In this example, the air sampler 102 can process the pathogen sample in the anomaly detection module to estimate a quantity of ATP present in the pathogen sample, which may be indicative of a quantity of living organisms (i.e., a microbe level) present in the pathogen sample and, therefore, in the conference room. In response to the quantity of ATP present in the pathogen sample exceeding a threshold quantity, the pathogen detection system 100 can signal (e.g., via activation of a light on the outer surface of the air sampler 102) detection of organic matter in the conference room above a standard level.

In one implementation, the air sampler 102 can be configured to activate the anomaly detection module for monitoring microbe levels within the environment at a high frequency (e.g., continuously, once every minute, once every ten minutes). For example, the air sampler 102 can continuously draw air through the inlet for collection of a pathogen sample on the sampling medium (e.g., a filter cassette, a charged plate) within the air sampler 102. The air sampler 102 can: extract a portion of this pathogen sample for transfer to the anomaly detection module of the detection subsystem at a frequency of 60 seconds; estimate a quantity of ATP in the portion of the pathogen sample via a UV light detector included in the anomaly detection module; and characterize a microbe level of this portion of the pathogen sample based on the quantity of ATP. Therefore, in this implementation, the air sampler 102 can leverage relatively low-resolution data (e.g., quantity of ATP in the pathogen sample) to semi-continuously (e.g., every 60 seconds) monitor changes in microbe levels in the environment, which may be indicative of a pathogen (e.g., virus, bacteria, fungi, pollen) presence in the environment In this implementation, the air sampler 102 can include the anomaly detection module to predict future microbe levels and/or pathogen presence in the environment based on changes in the organic load of pathogen samples over time. For example, the air sampler 102 can be configured to semi-continuously monitor pathogen samples at the anomaly detection module of the detection subsystem to semi-continuously estimate an organic load of pathogen samples collected from a particular environment. In particular, the air sampler 102 can: at a first time, estimate a first organic load of a pathogen sample extracted from air in the particular environment; at a second time succeeding the first time, estimate a second organic load of the pathogen sample; at a third time succeeding the second time, estimate a third organic load of the pathogen sample. Based on the first organic load, the second organic load, and the third organic load, the pathogen detection system 100 can estimate an integral of the organic load detected over time and leverage this integral to predict a fourth organic load of the pathogen sample at a future time succeeding the third time.

6.2.2 Second Detection Module: Predefined Pathogen Detection

In one implementation, the pathogen detection system 100 can be configured to detect presence of a set of predefined pathogens in pathogen samples collected from an environment. In this implementation, the pathogen detection system 100 can include the detection subsystem including a second detection module (or a "pathogen-specific detection module") configured to detect presence of the set of predefined pathogens. In particular, the pathogen-specific detection module can include a set of genetic detectors, each genetic detector in the set of genetic detectors configured to detect a previously defined pathogen via loop-mediated isothermal amplification. Therefore, in this implementation, the pathogen detection system 100 can implement a targeted molecular diagnostic approach to interpret whether pathogens from this set of predefined pathogens are present in the environment.

For example, the pathogen-specific detection module can include a set of genetic test-strips configured to detect a set of predefined pathogens (e.g., SARS-CoV-2, Influenza A, *E. Coli*) via loop-mediated isothermal amplification, each genetic test-strip corresponding to a predefined pathogen in the set of predefined pathogens. In this example, the pathogen detection system 100 can: trigger collection of a pathogen sample onto a sampling medium (e.g., a filter cartridge, a voltage collection plate) loaded within the air sampler 102 over a sampling period; trigger preparation and/or processing of the pathogen sample for genetic testing according to various genetic techniques (e.g., as described above) in response to expiration of the sampling period; trigger transferring of the pathogen sample to the pathogen-specific detection module of the detection subsystem within the air sampler 102; and trigger activation of the LAMP reaction via the set of genetic test-strips configured to detect presence of the set of predefined pathogens. In this example, each genetic test-strip can be configured to change color in response to detection of the corresponding predefined pathogen in the pathogen sample. Therefore, in response to detecting a color change in a first genetic test-strip corresponding to a first pathogen, in the set of predefined pathogens, the pathogen detection system 100 can detect presence of the first pathogen within the pathogen sample and therefore within the environment.

Alternatively, in the preceding example, in response to expiration of the sampling period, the pathogen detection system 100 can prompt a user associated with the environment to: collect the pathogen sample from the air sampler 102; and transfer the pathogen sample to the pathogen-specific detection module—external and/or remote from the air sampler 102 and loaded with the set of genetic test strips—for further processing and detection of the set of predefined pathogens via activation of the LAMP reaction at each genetic test strip in the set of genetic strips.

In one implementation, the genetic detector of the pathogen-specific detection module can be configured to detect a particular set of high-risk pathogens. For example, for a first instance of the air sampler 102 installed in a first geographical region, the pathogen-specific detection module can be configured to detect a first set of pathogens considered to be high-risk in this first geographical region. However, for a second instance of the air sampler 102 installed in a second geographical region remote from the first geographical region, the pathogen-specific detection module can be configured to detect a second set of pathogens—distinct from the first set of pathogens—considered to be high-risk in this second geographical region. In another example, for a first instance of the air sampler 102 installed in a restaurant, the pathogen-specific detection module can be configured to detect a first set of food-borne pathogens (e.g., *E. Coli, Campylobacter, Salmonella, Listeria*) considered to be high-risk in a restaurant. However, for a second instance of the air sampler 102 installed in an elementary school classroom, the pathogen-specific detection module can be configured to detect a second set of pathogens (e.g., *Staphylococcus aureus*, SARS-CoV-2, Influenza) considered to be high-risk in an elementary school.

In yet another example, during the summer, for an instance of the air sampler 102 installed in an office space, the pathogen-specific detection module can be configured to detect a first set of pathogens considered to be high-risk during the summer. However, during the winter, for the instance of the same pathogen detection system 100 installed in the office space, the pathogen-specific detection module can be reconfigured to detect a second set of pathogens considered to be high-risk during the winter.

In a similar example, the pathogen-specific detection module can be configured to detect different pathogens and/or different sets of pathogens over time, such as at different times of day, during different seasons, and/or based on risk associated with transmission of a particular pathogen. In particular, in this example, the pathogen detection system 100 can prompt a user (e.g., associated with the environment, associated with the pathogen-specific detection module) to load the pathogen-specific detection module with a first set of genetic detectors (e.g., a first set of genetic test strips) configured to detect a first set of pathogens at a first time. During a first time period succeeding the first time, the pathogen detection system 100 can then trigger collection of a series of pathogen samples (e.g., according to a target frequency) to monitor pathogen levels of the first set of pathogens during the first time period. Later, at a second time succeeding the first time period, the pathogen detection system 100 can prompt the user to: remove the first set of genetic detectors from the pathogen-specific detection module; and reload the pathogen-specific detection module with a second set of genetic detectors configured to detect a second set of pathogens. Then, during a second time period succeeding the second time, the pathogen detection system 100 can then trigger collection of a second series of pathogen samples (e.g., according to a target frequency) to monitor pathogen levels of the second set of pathogens during the second time period.

In this implementation, the air sampler 102 can be configured to activate the pathogen-specific detection module for detection of predefined pathogens within the environment at a moderate frequency (e.g., once per hour, once per day, once per week) relative the first stage of detection. For example, the air sampler 102 can: transfer a pathogen sample from the sampling media to the pathogen-specific detection module at a frequency of one hour; and, each hour, detect presence and/or absence of a set of predefined pathogens from the pathogen sample via loop-mediated isothermal amplification performed at the genetic detector. By running pathogen samples through the pathogen-specific detection module, the pathogen detection system 100 enables relatively quick (e.g., within one hour, within four hours) detection and identification of high-risk pathogens (e.g., SARS-CoV-2), therefore enabling a person(s) present in the office space to feel more confident and/or protected in the office space and enabling rapid action and/or mitigation responsive to detection of these high-risk pathogens.

6.2.3 Third Detection Module: Pathogen Profile Characterization

In one implementation, the pathogen detection system 100 can include a detection subsystem including a pathogen-profile detection module configured to characterize a pathogen profile of the pathogen sample. The pathogen-profile detection module can include a genetic sequencer (e.g., a DNA and/or RNA sequencing device) configured to enable genomic sequencing of each organism (e.g., virus, bacteria, fungi) present in the pathogen sample. Therefore, at the pathogen-profile detection module, the pathogen detection system 100 can identify each pathogen present in the pathogen sample based on the genome.

For example, the air sampler 102 can include the pathogen-profile detection module including a genetic sequencer configured to identify a complete genome for each organism detected in the pathogen sample. For each identified genome, the pathogen detection can: identify a particular pathogen matched to the genome; and generate a pathogen profile for the classroom based on each pathogen identified in the pathogen sample. The pathogen detection system 100 can then trigger generation and delivery of a notification of the pathogen profile to a user associated with the classroom.

In this implementation, the air sampler 102 can be configured to activate the pathogen-profile detection module for characterizing the pathogen profile of the pathogen sample at a lower frequency (e.g., once every four hours, once per day, once per week). For example, the air sampler 102 can continuously draw air through the inlet for collection of a pathogen sample on the sampling medium (e.g., a filter cassette, a charged plate) within the air sampler 102. The air sampler 102 can: extract a portion of this pathogen sample for transfer to the pathogen-profile detection module of the detection subsystem at a frequency of 24 hours; transfer the pathogen sample to the genetic sequencer of the pathogen-profile detection module for identification of a set of pathogens present in the pathogen sample; and characterize a pathogen profile of the pathogen sample based on the set of pathogens identified. Therefore, in this implementation, the pathogen detection system 100 can leverage relatively high-resolution data extracted at a lower frequency to identify each pathogen present in the environment.

6.2.4 Multiple Detection Stages

In one implementation, the pathogen detection system 100 can implement multiple stages of pathogen detection in order to more accurately interpret and predict pathogen levels (e.g., presence, magnitude) in the external field. In particular, the pathogen detection system 100 can selectively operate detection stages of the detection subsystem to increase accuracy and speed of pathogen detection while minimizing risk to users associated with and/or present in the environment. For example, the air sampler 102 can be configured to include: a anomaly detection module including a microbe detector configured to detect an organic load of a pathogen sample captured from an external field occupied by the air sampler 102; a pathogen-specific detection module including a selective pathogen detector configured to detect presence and/or magnitude of a particular set of pathogens in the pathogen sample via loop-mediated isothermal amplification (or "LAMP"); and/or a pathogen-profile detection module including a genetic sequencer configured to characterize a pathogen spectrum of the pathogen sample via nanopore sequencing. In particular, in this example, the pathogen detection system 100 can include these different stages to both detect baseline changes in levels of organic matter (i.e., microbe levels) present in the environment and to distinctly identify pathogens present in the environment. Therefore, in this implementation, the pathogen detection system 100 can combine low-resolution, high-frequency time series of non-specific microbe levels in the external field with higher-resolution, lower-frequency time series of specific pathogens of interest and/or all genomes in the external field to confirm, identify, and/or predict pathogen presence in the environment.

In one implementation, the air sampler 102 can be configured to include multiple detection stages within a single detection subsystem. In one example, the pathogen detection system 100 can include the first, second, and pathogen-profile detection modules as described above. At a first time, the air sampler 102 can pass a first pathogen sample through the anomaly detection module to estimate an organic load of the first pathogen sample. Then, in response to the organic load exceeding a threshold organic load, the pathogen detection system 100 can trigger activation of the pathogen-specific detection module and transfer the first pathogen sample from the anomaly detection module to the pathogen-specific detection module via the first handoff. The pathogen detection system 100 can then pass the first pathogen sample through the pathogen-specific detection module to test for a particular set of high-risk pathogens via the LAMP reaction at the genetic detector. In response to detecting a particular pathogen in the set of high-risk pathogens, the pathogen detection system 100—in conjunction with the computer system—can immediately notify a user (e.g., an administrator, a manager) of the particular pathogen detected. Alternatively, in response to detecting absence of each pathogen in the set of high-risk pathogens, the pathogen detection system 100 can trigger activation of the pathogen-profile detection module and transfer the first pathogen sample from the pathogen-specific detection module to the pathogen-profile detection module via a second handoff.

Alternatively, in another implementation, the pathogen detection system 100 can include a set of air sampler 102s 102, each air sampler 102 in the set of air sampler 102s 102 including a particular detection stage. For example, the pathogen detection system 100 can include: a first air sampler 102 including the anomaly detection module; a second air sampler 102 including the pathogen-specific detection module; and a third air sampler 102 including the pathogen-profile detection module.

6.2.4.1 Handoff Between Detection Stages

In one implementation, the pathogen detection system 100 can be configured to pass the pathogen sample through these detection stages in series. For example, the air sampler 102 can include: a first handoff configured to transfer the pathogen sample collected at the sampling medium the anomaly detection module; a second handoff configured to transfer the pathogen sample from the anomaly detection module to the pathogen-specific detection module; and a third handoff configured to transfer the pathogen sample from the pathogen-specific detection module to the pathogen-profile detection module. In this example, the air sampler 102 can: transfer a pathogen sample to the anomaly detection module via the first handoff; in response to estimating an organic load exceeding a threshold organic load at the anomaly detection module, transfer the pathogen sample from the anomaly detection module to the pathogen-specific detection module via the second handoff; and, in response to detecting absence of a set of predefined pathogens at the pathogen-specific detection module, transfer the pathogen sample from the pathogen-specific detection module to the pathogen-profile detection module via the third handoff. Therefore, in this example, by running the pathogen sample through the detection stages in series, the air sampler 102 enables selective activation of each detection stage. In particular, the air sampler 102 can minimize testing of the pathogen sample at the second and pathogen-profile detection modules based on data extracted from air in the anomaly detection module, thereby enabling further enrichment of the pathogen sample before transfer of the pathogen sample to these detection stages.

Additionally and/or alternatively, in this implementation, the pathogen detection system 100 can be configured to pass the pathogen sample through these stages in parallel. For example, the pathogen detection system 100 can include a set of inlets including: a first inlet configured to transfer a first portion of a pathogen sample to the anomaly detection module; a second inlet configured to transfer a second portion of the pathogen sample to the pathogen-specific detection module; and a third inlet configured to transfer a third portion of the pathogen sample to the pathogen-profile detection module. In this example, the pathogen detection system 100 enables faster identification of pathogens present in the pathogen sample (e.g., via the second and pathogen-profile detection modules).

6.3 Cleaning Module

The air sampler 102 can include a cleaning module configured to sanitize the air sampler 102—including the sampling medium—in preparation for the next sampling period.

For example, the pathogen detection system 100 can trigger collection of a first pathogen sample over a first sampling period. In response to termination of a first sampling period, the pathogen detection system 100 can trigger activation of the cleaning module—configured to sanitize surfaces of the air module to prevent contamination of pathogen samples (e.g., collected after the first pathogen sample)—during a cleaning cycle. Then, in response to receiving confirmation of completion of the cleaning cycle, the pathogen detection system 100 can trigger collection of a second pathogen sample during a second sampling period succeeding the first sampling period. The pathogen detection system 100 can therefore prevent or limit contamination to future pathogen samples collected within the air sampler 102 from the first pathogen sample by sanitizing surfaces of the air sampler 102, such as surfaces of the inlet, the air-capture module, the sampling medium, the set of detection modules, etc.

In one implementation, the cleaning module includes a sterilizing element configured to sterilize the air sampler 102 in order to minimize contamination of pathogen samples captured by the pathogen detection system 100. For example, an air sampler 102 can be installed in a classroom of a school. The air sampler 102 can include a filter cartridge configured to collect and concentrate a pathogen sample captured from air from the classroom. This filter cartridge may be contaminated (e.g., with pathogenic RNA and/or DNA) which may lead to false-positive results for pathogens detected in the pathogen sample. Therefore, to prevent contamination of the pathogen sample when collected at the filter cartridge, the air sampler 102 can include an Ultraviolet LED light (or "UV LED light") configured to sterilize the filter cartridge. The pathogen detection system 100 can be configured to activate this UV LED light for sterilization of the filter cartridge prior to collection of the pathogen sample.

Additionally, the pathogen detection system 100 can be configured to activate the sterilizing element after processing of pathogen samples in order to deactivate any living organisms (e.g., bacteria, viruses) present within the pathogen detection system 100—including on the sampling media and/or within the sample.

In one variation, the pathogen detection system 100 can include an external sanitization feature configured to sanitize the environment occupied by the air sampler 102. For example, the pathogen detection system 100 can include an Ultraviolet LED light (or "UV LED light") coupled to an outer surface air sampler 102. In this example, the pathogen detection system 100 can selectively activate the UV LED light to sanitize the external field responsive to pathogen detection within the external field.

7. Sampling Periods: Pathogen Sample Enrichment

The air sampler 102 can be configured to collect a pathogen sample over a particular sampling period of a target duration (e.g., one minute, one hour, 24 hours, 1 week) in order to enrich the pathogen sample during the sampling period. In particular, the air sampler 102 can continue to draw air from the environment and into the air sampler 102, for collection of the pathogen sample on the sampling medium, over a duration of the sampling period in order to increase a concentration of the pathogen sample for increased accuracy of pathogen detection via the detection subsystem.

Within this sampling period, the air sampler 102 can be configured to activate different detection modules of the detection subsystem at different frequencies (e.g., fixed or variable). For example, for an air sampler 102 including the anomaly detection module, the pathogen-specific detection module, and the pathogen-profile detection module, the pathogen detection system 100 can be configured to: activate the anomaly detection module at a first frequency (e.g., once every 30 seconds, once-per-minute, once every 10 minutes, once-per-hour); the pathogen-specific detection module at a second frequency (e.g., once-per-hour, once every 4 hours, once-per-day, once-per-week) less than the first frequency; and the pathogen-profile detection module at a third frequency (e.g., once-per-day, once-per-week, once every two weeks, once-per-month) less than the first frequency and/or less than the second frequency. The pathogen detection system 100 can therefore leverage data collected from each of these detection stages to interpret and/or model a pathogen profile for the environment over a period of time (e.g., one hour, one day, one week). Thus, the air sampler 102 can combine high-frequency, low-resolution data with low-frequency, high-resolution data to interpret an accurate (near) real-time pathogen profile of the environment.

7.1 Fixed Sampling Period

In one implementation, the air sampler 102 can be configured to operate according to a fixed sampling period.

In another example, the air sampler 102 can be configured to include: the anomaly detection module defining a first detection frequency of one minute; the pathogen-specific detection module defining a second detection frequency of one hour; and the pathogen-profile detection module defining a third frequency of eight hours. The detection subsystem can define a sampling period of eight hours (e.g., corresponding to the third frequency of the pathogen-profile detection module). Over the sampling period, the air sampler 102 can continue to collect the pathogen sample on the sampling medium while running the pathogen sample (e.g., a portion of the pathogen sample) through the anomaly detection module and pathogen-specific detection module at the first and second frequencies, respectively. Upon expiration of the sampling period, the air sampler 102 can pass the pathogen sample through the pathogen-profile detection module for complete genetic sequencing.

By waiting to pass the pathogen sample through the third stage until expiration of the sampling period, the air sampler 102 enables further enrichment of the pathogen sample, thereby enabling higher accuracy of detection of pathogens by the genetic sequencer. Further, this higher accuracy detection by the genetic sequencing enables higher accuracy characterization of the pathogen profile of the pathogen sample. Therefore, the pathogen detection system 100 can leverage this pathogen profile to confirm and/or negate errors in detection in the first and pathogen-specific detection modules.

For example, the air sampler 102 can trigger initiation of a first sampling period of ten hours at 8:00 AM. In this example, the air sampler 102 can include: the anomaly detection module defining a first detection frequency of one minute; the pathogen-specific detection module defining a second detection frequency of two hours; and the pathogen-profile detection module defining a third frequency of five hours. At 10:00 AM, the air sampler 102 can trigger activation of the pathogen-specific detection module for detection of pathogens in a set of high-risk pathogens. At this time, however, the pathogen sample may not be sufficiently enriched to enable accurate detection of the set of high-risk pathogens, and therefore yield a false-negative result. Later, at 12:00 PM, the air sampler 102 can again trigger activation of the pathogen-specific detection module for detection of pathogens in the set of high-risk pathogens. By this time, the pathogen sample may be more concentrated on the sampling medium and therefore, yield a positive result for a particular pathogen in the set of high-risk pathogens. Then, at 1:00 PM, the air sampler 102 can trigger activation of the pathogen-profile detection module for identification of a set of pathogens in the pathogen sample. In response to identifying the particular pathogen in the pathogen sample, the pathogen detection system 100 can confirm detection of the particular pathogen in the pathogen-specific detection module.

Therefore, in this implementation, the pathogen detection system 100 can leverage fixed sampling periods to enrich a particular pathogen sample over a fixed sampling period for enhanced pathogen detection and/or for confirmation of results (e.g., detection, identification). Upon termination of the fixed sampling period, the air sampler 102 can run the pathogen sample through the third stage of the detector module. Finally, the air sampler 102 can purge the pathogen sample and activate a cleaning module configured to sanitize the air sampler 102—including the sampling medium—in preparation for the next fixed sampling period.

7.1.1 Fixed Sampling Period: Single Detection Module

In one implementation, the pathogen detection system 100 can include a detection subsystem—such as integrated within the air sampler 102 and/or remote from the air sampler 102—including a single detection module (e.g., the anomaly detection module, the pathogen-specific detection module, or the pathogen-profile detection module). In this implementation, the air sampler 102 can collect a pathogen sample during a fixed sampling period of a target duration. In response to expiration of the fixed sampling period (e.g., expiration of the target duration), the air sampler 102 can: transfer the pathogen sample to the detection module for analysis; and trigger activation of the cleaning module in preparation for a next, fixed sampling period.

For example, the pathogen detection system 100 can include an air sampler 102 including: an air-capture module; and a detection subsystem including a pathogen-specific detection module integrated within the air sampler 102. In this example, the air sampler 102 can be configured to collect a pathogen sample over a fixed sampling period of a target duration (e.g., ten minutes, one hour, 24 hours). Then, in response to expiration of the target duration, the pathogen detection system 100 can: trigger termination of the first sampling period; and trigger the air sampler 102 to transfer the pathogen sample to the pathogen-specific detection module. Once genetic testing of the pathogen is complete, the pathogen detection system 100 can: access a set of pathogen data corresponding to results of genetic testing of the pathogen sample; and interpret presence of a set of pathogens in the environment based on the set of pathogen data. The pathogen detection system 100 can then trigger activation of the cleaning module within the air sampler 102 in preparation for collection of a next pathogen sample during a next sampling period.

The pathogen detection system 100 can similarly trigger collection and processing of pathogen samples during fixed sampling periods for an air sampler 102 including an anomaly detection module or a pathogen profile detection module.

Additionally and/or alternatively, the air sampler 102 can be configured to collect a sequence of pathogen samples across a sequence of fixed sampling periods within a global sampling period, each pathogen sample, in the sequence of pathogen samples, collected during a particular fixed sampling period, in the sequence of fixed sampling periods. For example, the pathogen detection system 100 can define a global sampling period of one week including a sequence of sampling periods defining a sampling frequency of once-per-weekday (e.g., one sampling period per weekday), each sampling period defining a target duration of 8 hours (e.g., between 9 AM and 5 PM). In this example, the air sampler 102 can: collect a first pathogen sample during a first sampling period on Monday; collect a second pathogen sample during a second sampling period on Tuesday; collect a third pathogen sample during a third sampling period on Wednesday; collect a fourth pathogen sample during a fourth sampling period on Thursday; and collect a fifth pathogen sample during a fifth sampling period on Friday. Between each sampling period, in the sequence of sampling periods, the air sampler 102 can trigger activation of the cleaning module to minimize contamination of the succeeding pathogen sample from the preceding pathogen sample. Alternatively, in the preceding example, the air sampler 102 can collect a single pathogen sample across the sequence of sampling periods during the sampling period in order to further enrich the pathogen sample. In this example, the air sampler 102 can trigger activation of the cleaning module in response to expiration of the global sampling period.

7.2 Dynamic Sampling Periods

Alternatively, in another implementation, the air sampler 102 can be configured to operate according to a dynamic sampling period. In this implementation, the air sampler 102 can be configured to selectively trigger activation of detection modules based on data (e.g., pathogen sample data, environmental data, time-based data) collected during the dynamic sampling period.

For example, the pathogen detection system 100 can be configured to include the detection subsystem including: the anomaly detection module; and the pathogen-specific detection module (e.g., within the air sampler 102, external the air sampler 102 and within the environment, or at a remote location). The air sampler 102 can be configured to automatically activate the anomaly detection module at a frequency of once per minute during a sampling period for a pathogen sample. In this example, in response to characterizing an organic load of the pathogen sample below the threshold organic load, the air sampler 102 can continue collection and passing of the pathogen sample through the anomaly detection module at the first frequency. However, in response to characterizing the organic load of the pathogen sample above the threshold organic load, the air sampler 102 can: flag the pathogen sample for further investigation; and trigger activation of the pathogen-specific detection module.

Additionally and/or alternatively, in this example, in response to characterizing the organic load of the pathogen sample above the threshold organic load, the pathogen detection system 100 can: access a threshold enrichment duration defined for pathogen samples collected in the environment; and compare a current duration of the sampling period to this threshold enrichment duration. Then, in response to the threshold enrichment duration exceeding the current duration, the pathogen detection system 100 can: continue triggering collection of the pathogen sample; and, in response to the threshold enrichment duration falling below the first duration, terminate the first sampling period and trigger activation of the pathogen-specific detection module. The pathogen detection system 100 can then interpret presence of a set of pathogens based on genetic analysis of the pathogen sample via the pathogen-specific detection module.

In response to detecting presence of a particular pathogen (e.g., above a threshold pathogen level) in a set of high-risk pathogens, the pathogen detection system 100 can notify a set of users (e.g., a user or a group of users) associated with the environment of detection of the particular pathogen in the environment.

Additionally, in another example, the detection subsystem can also include the pathogen-profile detection module. In this example, in response to detecting presence of the particular pathogen in the pathogen sample, the pathogen detection system 100 can automatically trigger activation of the pathogen-profile detection module to confirm presence of the particular pathogen in the pathogen sample. Additionally and/or alternatively, the air sampler 102 can trigger activation of the pathogen-profile detection module after a set duration (e.g., one hour, four hours), to ensure the pathogen sample is sufficiently enriched for accurate confirmation of presence of the particular pathogen. Finally, upon expiration of the sampling period (e.g., after passing the pathogen sample through the pathogen-profile detection module), the air sampler 102 can purge the pathogen sample and activate the cleaning module in preparation for the next sampling period.

Alternatively, in the preceding example, in response to characterizing the organic load of the pathogen sample above an upper threshold organic load greater than the threshold organic load in the anomaly detection module, the air sampler 102 can trigger activation of the pathogen-profile detection module due to the high organic load of the pathogen sample. Additionally, the air sampler 102 can trigger of the pathogen-specific detection module concurrently in order to more quickly identify a presence and/or absence of a particular high-risk pathogen. However, by activating both stages concurrently, the pathogen detection system 100 can enable faster detection and identification of pathogens present in the pathogen sample when the anomaly detection module detects a large organic load, which may be indicative of an increased pathogen presence.

In one variation, the air sampler 102 can be configured to operate according to both a dynamic sampling period and a fixed sampling period. For example, the air sampler 102 can define a fixed sampling period of twenty-four hours for a pathogen-profile detection module of the air sampler 102. In this example, the air sampler 102 can: transfer a pathogen sample to the anomaly detection module via the first handoff for estimating an organic load of the pathogen sample; and, in response to estimating an organic load exceeding a threshold organic load at the anomaly detection module, transfer the pathogen sample from the anomaly detection module to the pathogen-specific detection module via the handoff module to confirm presence and/or absence of a set of high-risk pathogens. Then, in response to detecting presence of a first high-risk pathogen, in the set of high-risk pathogens, the air sampler 102 can: notify an administrator associated with the environment of the presence of the first high-risk pathogen in the environment; and return to monitoring the pathogen sample at the first stage of detection. However, upon expiration of the twenty-four hour fixed sampling period, the air sampler 102 can automatically pass the pathogen sample to the pathogen-profile detection module to identify a complete pathogen profile for this pathogen sample. In this example, the pathogen detection system 100 can corroborate results from the first and pathogen-specific detection modules while providing a complete pathogen profile of the pathogen sample.

7.2.1 Dynamic Sampling Windows: Detection Triggers

The pathogen detection system 100 can be configured to selectively trigger collection of pathogen samples at the air sampler 102 for pathogen detection based on a set of detection triggers (or "detection rules") defined for the environment.

In particular, the pathogen detection system 100 can: monitor (or "track") a set of controls—such as time-based controls, organic matter levels, pathogen levels, and/or environmental controls (e.g., occupancy, carbon dioxide levels, air flow)—in the environment over time; and compare the set of controls to the defined detection triggers for this environment in real-time. For example, the pathogen detection system 100 can: continuously, semi-continuously, and/or periodically (e.g., according to a target frequency) access a set of control data, recorded by a set of sensors installed on the air sampler 102 and/or within the environment, to assemble a series (e.g., timeseries) of control data corresponding to the environment during a sampling period. During the sampling period, if the set of control data aligns with a particular detection trigger—such as if a current carbon dioxide level exceeds a threshold carbon dioxide level defined for the environment—in the set of detection triggers, defined for the environment, the pathogen detection system 100 can automatically trigger activation of a detection module of the detection subsystem and/or trigger collection of a pathogen sample for detection of a particular pathogen and/or a particular set of pathogens in the environment.

In one example, the pathogen detection system 100 can define a set of detection triggers including: a duration trigger defining a target duration of sampling periods (e.g., for a particular detection module); an organic load trigger defining threshold organic load of pathogen samples; an air temperature trigger defining a nominal temperature range of ambient air in an environment; an air pressure trigger defining a nominal pressure range of ambient air in an environment; and/or an occupancy trigger defining a threshold occupancy level in the environment. The pathogen detection system 100 can thus compare current control data extracted from the environment to these detection triggers to selectively activate the detection subsystem according to the set of detection triggers.

7.2.1.1 Pathogen Sample Detection

In one implementation, the pathogen detection system 100 can selectively trigger the air sampler 102 to collect a pathogen sample and/or activate a particular detection stage of the detection subsystem based on pathogen sample data (e.g., pathogen levels and/or anomaly detection) for pathogen samples previously or currently collected at the air sampler 102.

For example, the pathogen detection system 100 can selectively trigger the air sampler 102 to activate a particular detection module of the detection subsystem based on changes in organic matter levels (e.g., ATP levels)—representative of microbial levels—in the environment, as described above.

In another example, the pathogen detection system 100 can selectively adjust a target duration of a sampling period based on detection of a particular pathogen or set of pathogens in the environment during a preceding time period. For example, during a first sampling period of a first target duration, the pathogen detection system 100 can trigger collection of a first pathogen sample. In response to expiration of the first target duration, the pathogen detection system 100 can: terminate the first sampling period; and activate the pathogen-specific detection module for detection of a set of pathogens via genetic analysis. Then, during a second sampling period succeeding the first sampling period, in response to detection of a first pathogen, in the set of pathogens, in the first pathogen sample, the pathogen detection system 100 can: trigger collection of a second pathogen sample during the second sampling period of a second target duration less than the first target duration. Therefore, by reducing the duration of the second sampling period, the pathogen detection system 100 can minimize latency to detection of the second pathogen sample via the pathogen-specific detection module, and thereby minimize latency to possible detection of presence of the first pathogen in the second pathogen sample.

7.2.1.2 Environmental Controls

In one implementation, the pathogen detection system 100 can selectively trigger the air sampler 102 to collect pathogen samples and/or activate a particular detection stage of the detection subsystem—such as for pathogen detection via the pathogen detection stage and/or pathogen-profile detection module—based on changes in environmental controls in the environment.

For example, the pathogen detection system 100 can access a set of environmental data—recorded by a set of sensors installed on the air sampler 102 and/or within the environment containing the air sampler 102—such as: a set of occupancy data (e.g., a quantity of human occupants in the environment; an occupancy density in the environment, an duration of occupancy per human occupant present in the environment); a set of ambient air data (e.g., temperature of ambient air in the environment, a carbon dioxide level of ambient air in the environment, an oxygen level of ambient air in the environment, a pressure level of ambient air in the environment); a set of HVAC data (e.g., a rate of airflow in the environment, a rate of ventilation in the environment, a rate of heating or cooling in the environment, a current temperature); and/or a set of action data (e.g., a current activity level, a type of activity currently performed in the environment, a quantity of instances of a door opening, a quantity of instances of sink usage, a quantity of instances of a refrigerator opening) representing actions or tasks performed within the environment.

The pathogen detection system 100 can then leverage this environmental data to identify environmental changes within the environment associated with increased risk of exposure to a particular pathogen or set of pathogens in the environment.

For example, during a setup period, the pathogen detection system 100 can define a set of environmental triggers including: a threshold temperature (e.g., a maximum and/or minimum temperature); a threshold pressure level (e.g., a maximum and/or minimum air pressure); a threshold carbon dioxide level (e.g., a maximum and/or minimum carbon dioxide concentration); a threshold occupancy level (e.g., a maximum quantity of occupants, a maximum occupancy density); and/or a threshold airflow rate (e.g., a minimum air circulation rate, a minimum ventilation rate). Further, the pathogen detection system 100 can include a set of sensors—installed on the air sampler 102 and/or within the environment containing the air sampler 102—including: a temperature sensor configured to record a current air temperature within the environment; a pressure sensor configured to record a current air pressure within the environment; a carbon dioxide sensor configured to record a current carbon dioxide concentration of ambient air within the environment; an occupancy sensor configured to record a quantity of human occupants present in the environment; and an airflow sensor (e.g., integrated within an HVAC system installed in the environment) configured to record a current airflow rate in the environment.

Then, during a live period succeeding the setup period, the pathogen detection system 100 can access environmental data recorded by the set of sensors; and compare this environmental data to the set of environmental triggers to identify instances of increased risk of pathogen spread in the environment in (near) real time. In particular, in this example, at a first time within the live period, the pathogen detection system 100 can: access a first set of environmental data—including a first temperature, a first pressure level, a first carbon dioxide level, a first occupancy level, and a first airflow rate—recorded by the set of sensors at approximately (e.g., within a preceding time interval) the first time; and compare the first set of environmental data to the set of environmental triggers defined for the environment. In this example, in response to the first carbon dioxide level exceeding the threshold carbon dioxide level, the pathogen detection system 100 can: flag the environment for further evaluation based on detection of an environmental trigger, in the set of environmental triggers, in the environment; and trigger collection of a pathogen sample for detection of a set of predefined pathogens.

Alternatively, in response to detecting absence of the set of environmental triggers at the first time, the pathogen detection system 100 can: at a second time succeeding the first time by a set duration (e.g., 1 minute, 10 minutes, 1 hour), access a second set of environmental data—including a second temperature, a second pressure level, a second carbon dioxide level, a second occupancy level, and a second airflow rate—recorded by the set of sensors at approximately the second time; and compare the second set of environmental data to the set of environmental triggers.

7.2.1.3 Risk

In another implementation, the pathogen detection system 100 can selectively collect and/or process pathogen samples based on evaluated risk—associated with presence and/or transmission of a particular pathogen or set of pathogens—in the environment. In this implementation, the pathogen detection system 100 can characterize risk in the environment based on the set of controls in the environment including environmental controls, time-based controls, and/or historical pathogen sample detection, such as: a current time of day; a duration of time passed from expiration of a preceding sampling period; a detected pathogen level of a particular pathogen detected in a pathogen sample collected in the preceding sampling period; a current organic matter level (e.g., an amount of ATP detected in a current pathogen sample); a current carbon dioxide level of ambient air in the environment; a current temperature of ambient air in the environment; and/or a current pressure level of ambient air in the environment. The pathogen detection system 100 can be configured to continuously, semi-continuously, and/or periodically (e.g., according to a particular frequency) evaluate risk within the environment to inform sampling and pathogen detection.

For example, during a sampling period for a pathogen sample, the pathogen detection system 100 can: access a series of environmental data—such as including a series of occupancy data recorded by an occupancy sensor, a series of air temperature data recorded by a temperature sensor, and/or a series of carbon dioxide level data recorded by a carbon dioxide sensor—corresponding to the environment and recorded by a set of sensors arranged within the environment; characterize a risk level for the environment during the sampling period based on the series of environmental data; and, in response to the risk level exceeding a threshold risk defined for the environment, terminate the sampling period and interpret presence of a set of pathogens in the environment via genetic analysis of the pathogen sample (e.g., at or remote the air sampler 102).

In particular, in the preceding example, the pathogen detection system 100 can: access a threshold occupancy level defined for the environment; access a nominal air temperature range defined for the environment; and access a nominal carbon dioxide level range defined for the environment. The pathogen detection system 100 can then characterize the risk level for the environment based on the first series of occupancy data, the threshold occupancy level, the first series of air temperature data, the nominal air temperature range, the first series of carbon dioxide level data, and the nominal carbon dioxide level range. Additionally and/or alternatively, in this example, the pathogen detection system 100 can also leverage the organic load (e.g., detected by the anomaly detection module) of the pathogen sample, collected during the sampling period, to characterize the risk level in the environment.

The pathogen detection system 100 can therefore leverage these detectable environmental controls and/or changes to these controls to selectively escalate a resolution of detection based on risk associated with these environmental controls and/or changes to these environmental controls in this particular environment.

Alternatively, in another example, the pathogen detection system 100 can characterize risk in the environment outside of a sampling period to inform selective sampling of pathogen samples. For example, during an initial time period preceding a first sampling period, the pathogen detection system 100 can: access a series of environmental data corresponding to the environment and recorded by a set of sensors arranged within the environment; characterize a risk level for the environment during the initial time period based on the series of environmental data; and, in response to the risk level exceeding a threshold risk defined for the environment, trigger initiation of the first sampling period. The pathogen detection system 100 can therefore leverage detectable environmental controls and/or changes to these controls to selectively trigger initiation of sampling periods and/or collection of pathogen samples. The pathogen detection system 100 can therefore minimize operation of the air sampler 102 during periods associated with lower risk based on these environmental controls.

8. Reporting

The pathogen detection system 100 can be configured to communicate data (e.g., pathogen levels, pathogen identity) to a set of users associated with the environment in which the air sampler 102 is installed. In particular, the pathogen detection system 100 can include a communication module configured to transmit data and/or notifications to a remote server and/or a set of local devices associated with the set of users. For example, the air sampler 102 can include a wireless transceiver configured to connect to a set of wireless devices and to transmit various data to this device from the air sampler 102. In particular, in this example, the air sampler 102 can connect to a user's smartphone or tablet—executing a native pathogen tracking application—to deliver notifications and/or updates on pathogen levels and/or pathogens identified in the environment.

In one implementation, the communication module can be configured escalate a level of reporting data based on risk and/or sensitivity of the data. For example, the air sampler 102 can be configured to include a detection subsystem including the anomaly detection module and the pathogen-specific detection module. In this example, in response to characterizing a pathogen level (e.g., based on the organism load) for a pathogen sample above a threshold pathogen level in the anomaly detection module, the air sampler 102 can trigger activation of a light installed on an external surface of the body. By activating this light, the pathogen detection system 100 can alert a person(s) present in the environment of the increased pathogen level in the environment. Because data obtained from the anomaly detection module is relatively low-resolution and therefore relatively less sensitive, the pathogen detection system 100 can automatically trigger this "notification" visible to any person present in the environment. However, in response to detecting presence of a particular high-risk pathogen, in a set of high-risk pathogens, in the pathogen-specific detection module, the pathogen detection system 100 can automatically transmit a notification (e.g., via text message, via an automated voice message, via a native application executing on a user's mobile device) to an administrator associated with the environment. Because this data is higher-risk and/or more sensitive than data collected in the anomaly detection module, the pathogen detection system 100 can be configured to directly notify the administrator of the particular high-risk pathogen in near-real time upon detection. Additionally and/or alternatively, the pathogen detection system 100 can transmit a notification to users (e.g., via text message) that may have been exposed to the high-risk pathogen.

In one implementation, the pathogen detection system 100 can generate and transmit a prompt to the administrator including recommended actions for pathogen mitigation. For example, in response to detecting an increased organic load of low-risk pathogens (e.g., via the first and pathogen-profile detection modules), the pathogen detection system 100 can generate a prompt including a set of cleaning processes configured to reduce germs in the environment. In another example, in response to identifying a particular pathogen in an environment, the pathogen detection system 100 can generate a prompt including a safety protocol associated with the particular pathogen and/or a particular cleaning technique for mitigating the particular pathogen.

The pathogen detection system 100 and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for detecting pathogens in an environment comprising:
   during a first sampling period of a target duration:
      triggering collection of a first pathogen sample by an air sampler located in the environment and configured to draw ambient air from the environment through an inlet of the air sampler and onto a sampling medium within the air sampler for collection of pathogen samples; and
      tracking a first organic load of the first pathogen sample via a first detection module integrated within the air sampler and configured to detect organic matter present in pathogen samples; and
   in response to the first organic load exceeding a threshold organic load defined for the environment:
      flagging the first pathogen sample for further investigation;
      triggering activation of a second detection module, within the air sampler, configured to detect presence of the set of pathogens in the first pathogen sample via genetic analysis;
      accessing a set of pathogen data comprising results of genetic analysis of the first pathogen sample via the second detection module;
      interpreting presence of the set of pathogens in the environment during the first sampling period based on the set of pathogen data; and
      based on detecting presence of a first pathogen, in the set of pathogens, in the first pathogen sample:
         generating a first notification indicating presence of the first pathogen in the environment; and
         transmitting the first notification to a set of users associated with the environment.

2. The method of claim 1:
   wherein interpreting presence of the set of pathogens in the environment comprises, for each pathogen, in the set of pathogens, interpreting a pathogen level, in a set of pathogen levels, of the pathogen present in the first pathogen sample; and
   wherein generating the first notification indicating presence of the first pathogen in the environment based on detecting presence of the first pathogen in the first pathogen sample comprises:
      based on a first pathogen level of the first pathogen in the first pathogen sample exceeding a threshold pathogen level, defined for the first pathogen in the environment, detecting presence of the first pathogen in the first pathogen sample; and
      detecting presence of the first pathogen in the first pathogen sample, generating the first notification indicating presence of the first pathogen in the environment.

3. The method of claim 1:
   wherein tracking the first organic load of the first pathogen sample via the first detection module comprises:
      triggering activation of the first detection module at a fixed frequency during the first sampling period, the first detection module comprising an organic matter detector; and accessing the first organic load detected by the first detection module at the fixed frequency;
wherein triggering activation of the second detection module comprises:
 transferring the first pathogen sample to the second detection module within the air sampler; and
 triggering activation of a loop-mediated isothermal amplification reaction within a reaction vessel of the second detection module; and
wherein accessing the set of pathogen data comprises accessing the set of pathogen data recorded by a sensor arranged proximal the reaction vessel within the second detection module and configured to capture results of the loop-mediated isothermal amplification reaction.

4. The method of claim 1, further comprising, in response to detecting absence of each pathogen, in the set of pathogens, in the first pathogen sample:
 characterizing a difference between the first organic load and the threshold organic load;
 in response to the difference exceeding a threshold difference, flagging the first pathogen sample for further investigation; and
 in response to the difference falling below the threshold difference:
  generating a second notification indicating absence of each pathogen in the set of pathogens; and
  transmitting the second notification to the set of users.

5. The method of claim 1:
further comprising, at a first time, in response to the first organic load exceeding the threshold organic load, activating a second notification indicating detection of an organic load anomaly in the environment; and
wherein transmitting the first notification to the set of users comprises transmitting the first notification to the set of users at a second time succeeding the first time.

6. The method of claim 1, further comprising, during the first sampling period, in response to the first organic load remaining below the threshold organic load:
 continuing triggering collection of the first pathogen sample onto the sampling medium loaded in the air sampler; and
 in response to expiration of the target duration:
  terminating the first sampling period; and
  interpreting presence of the set of pathogens in the environment via genetic analysis of the first pathogen sample at the second detection module.

7. The method of claim 1, further comprising, in response to detecting absence of each pathogen, in the first set of pathogens, in the pathogen sample:
 flagging the first pathogen sample for further investigation;
 interpreting a first pathogen profile for the first pathogen sample based on genetic sequencing of the first pathogen sample via a third detection module configured to characterize pathogen profiles of pathogen samples; and
 in response to the first pathogen profile indicating presence of a second pathogen in the first pathogen sample:
  generating a second notification indicating presence of the second pathogen in the environment; and
  transmitting the second notification to the set of users.

8. The method of claim 1, wherein triggering collection of the first pathogen sample by the air sampler configured to draw ambient air from the environment through the inlet of the air sampler comprises triggering collection of the first pathogen sample by the air sampler configured to draw ambient air from the environment through the inlet of the air sampler comprising an air-capture module configured to draw air from the environment through the inlet of the air sampler and onto the sampling medium via electrostatic forces.

9. A method for detecting pathogens in an environment comprising:
during a first sampling period of a first target duration:
 triggering collection of a first pathogen sample from ambient air in the environment at an air sampler configured to draw ambient air from the environment, through an inlet of the air sampler, and onto a sampling medium loaded in the air sampler for collection of pathogen samples;
 tracking a first organic load of the first pathogen sample via a detection module integrated within the air sampler; and
 in response to the first organic load exceeding a threshold organic load defined for the environment prior to expiration of the first target duration:
  terminating the first sampling period; and
  detecting presence of a first pathogen, in a set of pathogens, in the environment via genetic analysis of the first pathogen sample; and
during a second sampling period succeeding the first sampling period and of a second target duration less than the first target duration:
 in response to detecting presence of the first pathogen in the environment during the first sampling period, triggering collection of a second pathogen sample from ambient air in the environment at the air sampler;
 tracking a second organic load of the second pathogen sample;
 in response to the second organic load remaining below the threshold organic load prior to expiration of the second target duration, continuing to trigger collection of the second pathogen sample; and
 in response to expiration of the second target duration:
  terminating the second sampling period; and
  interpreting presence of the set of pathogens in the environment via genetic analysis of the second pathogen sample.

10. The method of claim 9, further comprising:
in response to the first organic load exceeding the threshold organic load during the first sampling period, triggering activation of an alert indicating detection of an organic load anomaly in the environment; and
in response to detecting presence of the first pathogen:
 generating a notification indicating presence of the first pathogen in the environment; and
 transmitting the notification to a user associated with the environment.

11. The method of claim 9:
further comprising, during the first sampling period, tracking a first duration of the first sampling period; and
wherein terminating the first sampling period in response to the first organic load exceeding the threshold organic load prior to expiration of the first target duration comprises, in response to the first organic load exceeding the threshold organic load and in response to the first target duration exceeding the first duration:
 accessing a threshold enrichment duration defined for pathogen samples collected in the environment; and
 in response to the threshold enrichment duration exceeding the first duration:
  continuing triggering collection of the first pathogen sample; and in response to the threshold enrichment duration falling below the first duration, terminating the first sampling period.

12. The method of claim 9, wherein triggering collection of the first pathogen sample by the air sampler configured to draw ambient air from the environment through the inlet of the air sampler comprises triggering collection of the first pathogen sample by the air sampler configured to draw ambient air from the environment through the inlet of the air sampler comprising an air-capture module configured to draw air from the environment through the inlet of the air sampler and onto the sampling medium via a pump coupled to the inlet.

13. A method for detecting pathogens in an environment comprising:
- during an initial time period:
  - accessing a series of environmental data corresponding to the environment and recorded by a set of sensors arranged within the environment;
  - characterizing a risk level for the environment during the initial time period based on the series of environmental data; and
  - in response to the risk level exceeding a threshold risk defined for the environment, triggering initiation of a first sampling period of a target duration;
- during the first sampling period:
  - triggering collection of a first pathogen sample by an air sampler located in the environment and configured to draw ambient air from the environment through an inlet of the air sampler and onto a sampling medium within the air sampler for collection of pathogen samples; and
  - tracking a first organic load of the first pathogen sample via a first detection module integrated within the air sampler and configured to detect organic matter present in pathogen samples; and
- in response to the first organic load exceeding a threshold organic load defined for the environment:
  - flagging the first pathogen sample for further investigation;
  - interpreting presence of a set of pathogens in the environment based on genetic analysis of the first pathogen sample via a second detection module configured to detect presence of the set of pathogens in pathogen samples via genetic analysis; and
- in response to detecting presence of a first pathogen, in the set of pathogens, in the first pathogen sample:
  - generating a first notification indicating presence of the first pathogen in the environment; and
  - transmitting the first notification to a set of users associated with the environment.

14. The method of claim 13, wherein interpreting presence of the set of pathogens based on genetic analysis of the first pathogen sample via the second detection module comprises:
- terminating the first sampling period;
- prompting a user associated with the environment to collect the first pathogen sample from the air sampler for genetic analysis via the second detection module located in a secondary location remote from the environment;
- accessing a set of pathogen data comprising results of genetic analysis of the first pathogen sample via the second detection module; and
- interpreting presence of the set of pathogens in the environment during the first sampling period based on the set of pathogen data.

15. A method for detecting pathogens in an environment comprising:
- during a first sampling period of a target duration:
  - triggering collection of a first pathogen sample by an air sampler located in the environment and configured to draw ambient air from the environment through an inlet of the air sampler and onto a sampling medium within the air sampler for collection of pathogen samples; and
  - tracking a first organic load of the first pathogen sample via a first detection module integrated within the air sampler and configured to detect organic matter present in pathogen samples;
- during the first sampling period, in response to the first organic load exceeding a threshold organic load defined for the environment:
  - flagging the first pathogen sample for further investigation;
  - interpreting presence of a set of pathogens in the environment based on genetic analysis of the first pathogen sample via a second detection module configured to detect presence of the set of pathogens in pathogen samples via genetic analysis; and
  - in response to detecting presence of a first pathogen, in the set of pathogens, in the first pathogen sample:
    - generating a first notification indicating presence of the first pathogen in the environment; and
    - transmitting the first notification to a set of users associated with the environment; and
- during the first sampling period, in response to the first organic load remaining below the threshold organic load:
  - continuing triggering collection of the first pathogen sample onto the sampling medium loaded in the air sampler; and
  - in response to expiration of the target duration:
    - terminating the first sampling period;
    - interpreting presence of the set of pathogens in the environment via genetic analysis of the first pathogen sample at the second detection module; and
    - in response to terminating the first sampling period, triggering activation of a cleaning module within the air sampler during a first cleaning cycle, the cleaning module configured to sanitize surfaces of the air module to prevent contamination of pathogen samples.

16. The method of claim 15, further comprising, in response to confirming completion of the first cleaning cycle:
- triggering collection of a second pathogen sample by the air sampler during a second sampling period succeeding the first sampling period;
- tracking a second organic load of the second pathogen sample via the first detection module during the second sampling period; and
- in response to the second organic load exceeding the threshold organic load:
  - flagging the second pathogen sample for further investigation;
  - interpreting presence of the set of pathogens in the environment via genetic analysis of the second pathogen sample at the second detection module.

17. A method for detecting pathogens in an environment comprising:
- during a first sampling period of a target duration:
  - triggering collection of a first pathogen sample by an air sampler located in the environment and configured to draw ambient air from the environment through an inlet of the air sampler and onto a sampling medium within the air sampler for collection of pathogen samples; and tracking a first organic load of the first pathogen sample via a first detection module integrated within the air sampler and configured to detect organic matter present in pathogen samples;

in response to the first organic load exceeding a threshold organic load defined for the environment:

flagging the first pathogen sample for further investigation;

interpreting presence of a set of pathogens in the environment based on genetic analysis of the first pathogen sample via a second detection module configured to detect presence of the set of pathogens in pathogen samples via genetic analysis; and in response to detecting presence of a first pathogen, in the set of pathogens, in the first pathogen sample:

generating a first notification indicating presence of the first pathogen in the environment; and transmitting the first notification to a set of users associated with the environment; and in response to detecting absence of each pathogen, in the set of pathogens, in the first pathogen sample:

flagging the first pathogen sample for further investigation;

interpreting a first pathogen profile for the first pathogen sample based on genetic sequencing of the first pathogen sample via a third detection module configured to characterize pathogen profiles of pathogen samples; and in response to the first pathogen profile indicating presence of a second pathogen in the first pathogen sample:

generating a second notification indicating presence of the second pathogen in the environment; and transmitting the second notification to the set of users.

18. A method for detecting pathogens in an environment comprising:

during a first sampling period of a first target duration:

triggering collection of a first pathogen sample from ambient air in the environment at an air sampler configured to draw ambient air from the environment, through an inlet of the air sampler, and onto a sampling medium loaded in the air sampler for collection of pathogen samples;

tracking a first organic load of the first pathogen sample via a detection module integrated within the air sampler;

tracking a first duration of the first sampling period; and in response to the first organic load exceeding a threshold organic load defined for the environment and in response to the first target duration exceeding the first duration:

accessing a threshold enrichment duration defined for pathogen samples collected in the environment; and in response to the threshold enrichment duration exceeding the first duration:

continuing triggering collection of the first pathogen sample; and in response to the threshold enrichment duration falling below the first duration:

terminating the first sampling period; and interpreting presence of a set of pathogens in the environment via genetic analysis of the first pathogen sample; and during a second sampling period of a second target duration:

triggering collection of a second pathogen sample from ambient air in the environment at the air sampler;

tracking a second organic load of the second pathogen sample;

in response to the second organic load remaining below the threshold organic load prior to expiration of the second target duration, continuing to trigger collection of the second pathogen sample; and in response to expiration of the second target duration:

terminating the second sampling period; and interpreting presence of the set of pathogens in the environment via genetic analysis of the second pathogen sample.

19. A method for detecting pathogens in an environment comprising:

during a first sampling period of a first target duration:

triggering collection of a first pathogen sample from ambient air in the environment at an air sampler configured to draw ambient air from the environment, through an inlet of the air sampler, and onto a sampling medium loaded in the air sampler for collection of pathogen samples;

tracking a first organic load of the first pathogen sample via a detection module integrated within the air sampler;

in response to the first organic load exceeding a threshold organic load defined for the environment prior to expiration of the first target duration:

terminating the first sampling period; and interpreting presence of a set of pathogens in the environment via genetic analysis of the first pathogen sample;

accessing a first series of environmental data corresponding to the environment and recorded by a set of sensors arranged within the environment;

characterizing a first risk level for the environment during the first sampling period based on the first series of environmental data; and in response to the first risk level exceeding a threshold risk defined for the environment:

terminating the first sampling period; and interpreting presence of the set of pathogens in the environment via genetic analysis of the first pathogen sample; and during a second sampling period of a second target duration:

triggering collection of a second pathogen sample from ambient air in the environment at the air sampler;

tracking a second organic load of the second pathogen sample;

in response to the second organic load remaining below the threshold organic load prior to expiration of the second target duration, continuing to trigger collection of the second pathogen sample;

accessing a second series of environmental data corresponding to the environment and recorded by the set of sensors;

characterizing a second risk level for the environment during the second sampling period based on the second series of environmental data;

in response to the second risk level exceeding the threshold risk:

terminating the second sampling period; and
interpreting presence of the set of pathogens in the environment via genetic analysis of the second pathogen sample; and in response to expiration of the second target duration:
terminating the second sampling period; and
interpreting presence of the set of pathogens in the environment via genetic analysis of the second pathogen sample.

20. The method of claim 19:
wherein accessing the first series of environmental data recorded by the set of sensors comprises:
accessing a first series of occupancy data recorded by an occupancy sensor;
accessing a first series of air temperature data recorded by a temperature sensor; and
accessing a first series of carbon dioxide level data recorded by a carbon dioxide sensor; and
wherein characterizing the first risk level based on the first series of environmental data comprises:
accessing a threshold occupancy level defined for the environment;
accessing a nominal air temperature range defined for the environment;
accessing a nominal carbon dioxide level range defined for the environment; and
characterizing the first risk level based on the first series of occupancy data, the threshold occupancy level, the first series of air temperature data, the nominal air temperature range, the first series of carbon dioxide level data, and the nominal carbon dioxide level range.

* * * * *